United States Patent
Alcantar et al.

(10) Patent No.: US 9,776,895 B2
(45) Date of Patent: Oct. 3, 2017

(54) CACTUS MUCILAGE AND FERRIC IONS FOR THE REMOVAL OF ARSENATE (AS(V)) FROM WATER

(71) Applicants: Norma A. Alcantar, Tampa, FL (US); Dawn I. Fox, East Bank Demerara (GY)

(72) Inventors: Norma A. Alcantar, Tampa, FL (US); Dawn I. Fox, East Bank Demerara (GY)

(73) Assignee: University of South Florida, Tampa, FL (US)

( * ) Notice: Subject to any disclaimer, the term of this patent is extended or adjusted under 35 U.S.C. 154(b) by 258 days.

(21) Appl. No.: 14/206,404

(22) Filed: Mar. 12, 2014

(65) Prior Publication Data
US 2014/0190898 A1 Jul. 10, 2014

Related U.S. Application Data

(63) Continuation of application No. PCT/US2012/055477, filed on Sep. 14, 2012.
(Continued)

(51) Int. Cl.
*B01D 21/01* (2006.01)
*C02F 1/52* (2006.01)
(Continued)

(52) U.S. Cl.
CPC .......... *C02F 1/5263* (2013.01); *B01D 21/01* (2013.01); *C02F 1/5245* (2013.01);
(Continued)

(58) Field of Classification Search
None
See application file for complete search history.

(56) References Cited

U.S. PATENT DOCUMENTS

| 7,314,569 B2 * | 1/2008 | Cadena C. ............... B01J 20/06 210/681 |
| 7,943,049 B1 * | 5/2011 | Alcantar ............... C02F 1/5263 210/728 |
| 2009/0111694 A1 | 4/2009 | Dituro |

FOREIGN PATENT DOCUMENTS

WO  WO2008135920 A2  11/2008

OTHER PUBLICATIONS

Cardenas et al. (Carbohydrate Polymers, 2008, 73, 212-222).*
(Continued)

*Primary Examiner* — Clare Perrin
(74) *Attorney, Agent, or Firm* — Michele L. Lawson; Robert J. Varkonyi; Smith & Hopen, P.A.

(57) ABSTRACT

Potable drinking water is plagued with widespread arsenic contamination, particularly in developing communities. Ferric ions were introduced to interact with arsenate based on the strong affinity of arsenate for ferric hydroxides, followed by mucilage addition. The mucilage coagulated and flocculated the ferric-arsenate complex and formed visible flocs that settled at the bottom of the tubes. The system showed 75-96% arsenate removal in 1 hour, while longer retention times showed 100% removal. The role of the mucilage was demonstrated by untreated solutions showing no concentration difference and remaining stable for more than 15 days. This mucilage-based technology has the potential to be a relatively inexpensive, environmentally sustainable alternative to synthetic polymer flocculants for removing arsenic from drinking water.

21 Claims, 15 Drawing Sheets

Related U.S. Application Data

(60) Provisional application No. 61/534,494, filed on Sep. 14, 2011.

(51) Int. Cl.

| | |
|---|---|
| *B03D 3/00* | (2006.01) |
| *A61K 36/33* | (2006.01) |
| *C02F 1/56* | (2006.01) |
| *A61K 36/00* | (2006.01) |
| *C02F 1/00* | (2006.01) |
| *B01D 21/00* | (2006.01) |
| *C02F 1/62* | (2006.01) |
| *C02F 1/28* | (2006.01) |
| *C02F 101/10* | (2006.01) |

(52) U.S. Cl.
CPC .............. *C02F 1/5272* (2013.01); *C02F 1/56* (2013.01); *A61K 36/33* (2013.01); *C02F 1/286* (2013.01); *C02F 1/5236* (2013.01); *C02F 1/62* (2013.01); *C02F 2101/103* (2013.01)

(56) References Cited

OTHER PUBLICATIONS

Buttice et al. (Environ. Sci. Technol., 2010, 44, 3514-3519).*
Amin, et al. The mucilage of Opuntia ficus-indica Mill. Carbohydrate Research 1970, 15, 159-161.
Buttice, et al. Removal of Sediment and Bacteria from Water Using Green Chemistry. Environmental Science & Technology 2010, 44, (9), 3514-3519.
Cardenas, et al (1997). "Rheology and aggregation of cactus (*Opuntia ficus-indica*) mucilage in solution." Journal of the Professional Association for Cactus Development 2: 152-159.
Cardenas and Goycoolea, et al. (2008). "On the gelling behaviour of 'nopal' (Opuntia ficus indica) low methoxyl pectin." Carbohydrate Polymers 73(2): 212-222.
Dixit and Hering (2003). "Comparison of Arsenic(V) and Arsenic(III) Sorption onto Iron Oxide Minerals: Implications for Arsenic Mobility." Environmental Science & Technology 37(18): 4182-418.
Forni, et al. A preliminary characterization of some pectins from quince fruit (*Cydonia oblonga* Mill.) and prickly pear (*Opuntia ficus-indica*) peel. Carbohydrate Polymers 1994, 23, 231-234.
Ghebremichael, et al. A simple purification and activity assay of the coagulant protein from Moringa oleifra seed. Water Res. 2005, 39: 2338-2344.
Ghebremichael, et al. Combined natural organic and synthetic inorganic coagulants for surface water treatment. J Water Supply: Res and Tech—Aqua. 2009, 58(4): 267-276.
Ghebremichael, et al. Moringa oleifra: a natural coagulant, adsorbent and filter aid. Water quality Technology Conference, Cincinnati, Ohio Nov. 16-20, 2008.
Giles, et al., Iron and aluminium based adsorption strategies for removing arsenic from water. J Environmetnal Management 2011, 92, 3011-3022.
McGarvie & Parolis. The mucilage of Opuntia ficus-indica. Carbohydrate Research 1979, 69, (1), 171-179.
Medina-Torres, et al. (2000). "Rheological properties of the mucilage gum (*Opuntia ficus indica*)." Food Hydrocolloids 14: 417-424.
Miller, et al. Toward understanding the efficacy and mechanism of *Opuntia* spp. as a natural coagulant for potential application in water treatment. Environmental Science & Technology 2008, 42, (12), 4274-4279.
Paulsen & Lund. Water-soluble polysaccharides of Opuntia ficus-indica cv "Burbank's spineless". Phytochemistry 1979, 18, 569-571.
Saag, et al. Cactaceae mucilage composition. Journal of the Science of Food and Agriculture 1975, 26, 993-1000.
Tenny and Adams, Ferric salt reduce arsenic in mine effluent by combining chemical and biological treatment. Environ Science and Engineering. Jan. 2001.
Trachtenberg & Mayer. Composition and properties of Opuntia ficus-indica mucilage. Phytochemistry 1981, 20, (12), 2665-2668.
Turquois, et al. Extraction of highly gelling pectic substances from sugar beet pulp and potato pulp: influence of extrinsic parameters on their gelling properties. Food Hydrocolloids 1999, 13, (3), 255-262.
Young, et al. Using the Mexican cactus as a natural-based process for removing contaminants in drinking water. Abstracts of Papers American Chemical Society 2005, 230, U3767.
International Search Report and Written Opinion issued by the International Searching Authority dated Feb. 14, 2013 for International Patent Application No. PCT/US2012/055477.
International Preliminary Report on Patentability issued by the International Bureau dated Mar. 27, 2014 for International Patent Application No. PCT/US2012/055477.
Non-final office action issued by the USPTO dated Apr. 21, 2010 for U.S. Appl. No. 11/934,932.
Non-final office action issued by the USPTO dated Oct. 20, 2010 for U.S. Appl. No. 11/934,932.
Non-final office action issued by the USPTO dated Aug. 4, 2011 for U.S. Appl. No. 13/088,918.
Final office action issued by the USPTO dated Apr. 11, 2012 for U.S. Appl. No. 13/088,918.
Non-final office action issued by the USPTO dated Sep. 19, 2013 for U.S. Appl. No. 13/088,918.
Benjamin et al. "Water Chemistry." Illinois, 2002, Waveland Press.
Fox, et al., Removing Heavy Metals in Water: The Interaction of Cactus Mucilage and Arsenate (As (V)). Environ Sci. Technol. Mar. 8, 2012; 46(8):4553-9.
Fox, et al., Combining Ferric Salt and Cactus Mucilage for Arsenic Removal from Water. Environ. Sci. Technol. Mar. 1, 2016; 50(5):2507-13.

* cited by examiner

CACTUS MUCILAGE AND FERRIC IONS FOR THE REMOVAL OF ARSENATE (AS(V)) FROM WATER

CROSS-REFERENCE TO RELATED APPLICATIONS

This application is a continuation of and claims priority to International Patent Application No. PCT/US2012/055477, entitled: "Cactus Mucilage and Ferric Ions for the Removal of Arsenate (AS(V)) from Water," filed on Sep. 14, 2012 which is a non-provisional of and claims priority to U.S. Provisional Patent Application No. 61/534,494, with the same title, filed on Sep. 14, 2011, the contents of which are herein incorporated by reference.

GOVERNMENT SUPPORT STATEMENT

This invention was made with government support under Grant Numbers 1034849 and 1057897 awarded by the National Science Foundation. The government has certain rights in the invention.

FIELD OF THE INVENTION

This invention relates to arsenic removal from potable water. Specifically, the invention discloses using cactus mucilage, a natural hydrocolloid, as a coagulant aid and flocculant for a system using iron-based coagulation to remove arsenic from water.

BACKGROUND OF THE INVENTION

Arsenic contamination of groundwater has been recognized as a global public health problem since the 1990s, especially in developing communities without access to conventional water treatment facilities, with an estimated 70 million affected. Health issues were initially observed due to skin lesions and other health effects of large populations in Bangladesh and West Bengal, India, which was correlated to high levels of arsenic in their drinking water. Bangladesh, India, and Nepal have experienced a massive epidemic from arsenic groundwater contamination, partially due to installed tube wells to collect groundwater and prevent the indigenous populations from using bacteria-contaminated surface water. However, testing has revealed one in five of the tube wells are contaminated by water containing ten to fifty times the arsenic levels considered safe by the World Health Organization. Further, high levels of arsenic are found in water sources around the world, including Argentina, Chile, Canada, Mexico and the US, as seen in FIG. 1. Consumption of water with arsenic levels higher than 10 µg/L has been associated with arsenic poisoning (arsenicosis), though affected areas may see levels as high as 48,0000 µg/L, as seen in Table 1. However, with the exception of drinking water consumers from private and public wells in the Western US (Kumar, Adak et al. 2010), arsenicosis is not a major public health concern in most developed countries. This is because the arsenic removal technologies employed in developed countries, namely precipitation (coagulation-flocculation-sedimentation), lime softening, adsorption, ion exchange, membrane filtration, electrodialysis reversal and electrocoagulation, are not accessible to developing communities.

TABLE 1

A compilation of arsenic levels in groundwater around the world.*

| Country | Arsenic Concentration (µg/L) | Estimated population Exposed |
|---|---|---|
| Argentina | 1-9,900 | 200,000-2,000,000 |
| Bangladesh | <1-2500 | 57,000,000 at >10 µg/L |
| Chile | 100-1000 | 400,000 |
| China (Mongolia) | 40-4440 | 5,600,000 |
| China (Xinjiang) | 0.05-850 | >500 |
| Hungary | <2-176 | 400,000 |
| India (West Bengal) | <1-3700 | 6,000,000 |
| Mexico (Region Lagunera) | 8-624 | 400,000 |
| Nepal | <10-340 | 3,190,000 at >10 µg/L |
| Taiwan | 10-1820 | 100,000-200,000 |
| USA (Western USA) | 48,000 | — |
| USA (Southern Iowa and western Missouri) | 34-490 | — |
| UK | <1-80 | — |
| Vietnam (Hanoi) | 1-3100 | >1,000,000 |

*Adapted from (Mandal and Suzuki (2002). "Arsenic round the world: a review." Talanta 58: 201-235; Nordstrom, D. K. (2002). "Worldwide occurrences of arsenic in ground water." Science 296(5576); Garelick, et al. (2005). "Remediation technologies for arsenic contaminated drinking waters." J of Soils & Sediments 5(3): 182-190; Mondal, et al. (2006). "Laboratory based approaches for Arsenic remediation from contaminated water: Recent developments." J of Haz Mat B137: 464-479)

Arsenic is a metalloid with similar properties to phosphorus. Arsenic oxidizes to form hygroscopic, colorless, odorless $As_2O_3$ and $As_2O_5$. The principal means of arsenic dispersion through nature is via water, and varies from locations based on soil and arsenic forms. Arsenic has been attributed to changes in respiratory, gastrointestinal, hematopoietic, and cardiovascular systems. Because of the similarities between arsenic and phosphorus, arsenic can substitute in place of phosphorus in some biological reactions, making it poisonous. Particularly, consumption of arsenic-contaminated water may enter the metabolic citric cycle, inhibiting succinate dehydrogenase and preventing ATP production. Arsenic poisoning is cumulative and symptoms include nausea, vomiting, stomach aches, diarrhea, and delirium, skin lesions and cancers, cancers of the kidneys, bladder, lungs and liver, hyper-pigmentation and hyperkeratosis, and gangrene ("black foot disease"). Consequently, considerable effort has been put forth to reduce and mitigate exposure to arsenic-contaminated drinking water in affected communities.

Many technologies exist to remove arsenic from drinking water. These include precipitation (coagulation-flocculation-sedimentation), lime softening, adsorption, ion exchange, membrane filtration, phytoremediation, electrodialysis reversal and electrocoagulation. The strong affinity of iron compounds for arsenic is exploited in adsorption and precipitation systems. Of these two, precipitation (coagulation-flocculation-sedimentation or CFS) is popular because it is a relatively simple technology with low capital cost and depends on ferric salts which are common, easily found and relatively inexpensive. In CFS, the arsenic is removed by several mechanisms: the conversion of dissolved arsenate and arsenite to solid ferric arsenate and ferric arsenite phases, as well as adsorption and entrapment in hydrous ferric oxide phases. Typically ferric chloride or sulphate is used. The ferric salt facilitates floc formation, which leads to settling and sedimentation of the solid arsenic-bearing precipitate. However, ferric arsenate is relatively soluble (Tenny and Adams, Ferric salt reduce arsenic in mine effluent by combining chemical and biological treatment. Environ Science and Engineering. January 2001), and takes significant amounts of time to precipitate from solution. In some instances, coagulant aids are used to enhance floc formation by producing larger, denser flocs, which settle faster and shorten the sedimentation time. Further, the use of coagulant aids also decreases the dosage of coagulant needed. The coagulant aids are typically synthetic organic polyionic polymers, e.g. MAGNAFLOC, that function as bridges between microfloc particles (source). Recently, there has been an interest in using natural coagulants, flocculants and coagulant aids. The advantages of natural flocculants are that they are generally less toxic, more environmentally friendly, biodegradable and in some instances cheaper and more abundant than synthetic flocculants (Ghebremichael, et al. A simple purification and activity assay of the coagulant protein from *Moringa oleifra* seed. Water Res. 2005, 39: 2338-2344; Ghebremichael, et al. Combined natural organic and synthetic inorganic coagulants for surface water treatment. J Water Supply: Res and Tech-Aqua. 2009, 58(4): 267-276; Ghebremichael, et al. *Moringa oleifra*: a natural coagulant, adsorbent and filter aid. Water quality Technology Conference, Cincinnati, Ohio Nov. 16-20, 2008; Ghebremichael, et al. *Moringa oleifera* for simultaneous coagulation and disinfection in water purification. 57 Can Water Resources Assn Ann Congr., Montreal, Qc, CA, Jun. 16-18, 2004).

Most plant species produce an exopolysaccharide, a polymer of mono- and polysaccharides and proteins bonded by glycosidic bonds, referred to as mucilage. Plants secrete the substance to slow water loss, aid germination, and store food. The tuna cactus (*Opuntia ficus indica*) mucilage produced by the flattened pads of this cactus was of particular interest, of complex carbohydrates forming a neutral mixture of approximately 55 high-molecular weight sugar residues composed basically of arabinose, galactose, rhamnose, xylose, and galacturonic acid. The mucilage has the capacity to interact with metals, cations and biological substances. Importantly, mucilage swells in water but is insoluble. As such, the substance has the potential to precipitate ions, bacteria and particles from aqueous solutions. Further, the material has unique surface active characteristics, making it an ideal candidate for enhancing dispersion properties, creating emulsifications, and reducing surface tension of high polarity liquids.

This creates a need for accessible technologies, which are relatively inexpensive, reliable, robust, made from available, abundant materials for removing water contaminants, such as (As(V)), and which require little or no fossil fuel energy to work.

SUMMARY OF THE INVENTION

Cactus mucilage, extracted from the *Opuntia ficus-indica* (also known as Nopal and Prickly Pear cactus), is a clear, colorless thick liquid expressed by cut cactus pads comprising a mixture of sugars and carbohydrate polymers. The cactus mucilage is a natural hydrocolloid and flocculant shown to interact with dissolved heavy metals, such as arsenate. Several extracts are obtainable, including the non-gelling extract (NE) and the gelling extract (GE), which was used in this invention. This natural, environmentally-benign material is abundant and obtained through sustainable agriculture. The NE is the clear, colorless carbohydrate polymer secreted when the pad is cut, comprising mainly L-arabinose, D-galactose, L-rhamnose and D-xylose as well as galacturonic acid (Amin, et al. The mucilage of *Opuntia ficus-indica* Mill. Carbohydrate Research 1970, 15, 159-161; Forni, et al. A preliminary characterization of some pectins from quince fruit (*Cydonia oblonga* Mill.) and prickly pear (*Opuntia ficus-indica*) peel. Carbohydrate Polymers 1994, 23, 231-234; McGarvie & Parolis. The mucilage of *Opuntia ficus-indica*. Carbohydrate Research 1979, 69, (1), 171-179; Paulsen & Lund. Water-soluble polysaccharides of *Opuntia ficus-indica* cv "Burbank's spineless". Phytochemistry 1979, 18, 569-571; Saag, et al. Cactaceae mucilage composition. Journal of the Science of Food and Agriculture 1975, 26, 993-1000; Trachtenberg & Mayer. Composition and properties of *Opuntia ficus-indica* mucilage. Phytochemistry 1981, 20, (12), 2665-2668). The GE is a pectin, forming a structural component of the cell wall which is chemically similar to citrus pectin (Cardenas, et al. On the gelling behaviour of 'nopal' (*Opuntia ficus indica*) low methoxyl pectin. Carbohydrate Polymers 2008, 73, (2), 212-222).

The extracts have been shown to flocculate particles and bacteria, as well as interact with arsenic (Buttice, et al. Removal of Sediment and Bacteria from Water Using Green Chemistry. Environmental Science & Technology 2010, 44, (9), 3514-3519; Miller, et al. Toward understanding the efficacy and mechanism of *Opuntia* spp. as a natural coagulant for potential application in water treatment. Environmental Science & Technology 2008, 42, (12), 4274-4279; Young, et al. Using the Mexican cactus as a natural-based process for removing contaminants in drinking water. Abstracts of Papers American Chemical Society 2005, 230, U3767). In order to optimize this natural system, ferric ions were introduced to interact with arsenate based on the strong affinity of arsenate for ferric hydroxides.

A viable method of removing arsenic contamination from a sample of water was identified from this work. To remove arsenic contamination, a sample of water contaminated with arsenic was obtained and dosed with a ferric salt. The ferric ions interact with arsenate based on the strong affinity of arsenate for ferric hydroxides. Particularly useful ferric salts are provided in Table 2. The water was then allowed to sit for a time sufficient to permit the ferric salt to interact with the arsenic. Exemplary sitting times are at least 10 min, about 1 hour, and about 24 hours, such as 1 hour, 8 hours, 12 hours, 18 hours, and 24 hours.

TABLE 2

A list of the different ferric salts useful in the present invention.

| Ferric salt | Chemical composition |
| --- | --- |
| ferric carbonate | $Fe_2(CO_3)_3$ |
| ferric chloride | $Cl_3Fe$ |
| ferric fluoride | $FeF_3$ |
| ferric gluconate | $C_{18}H_{33}FeO_{21}$ |
| ferric hydroxide | $Fe(OH)_3$ |
| ferric nitrate | $Fe(NO_3)_3$ |
| ferric oxalate | $C_6H_2Fe_2O_{13}$ |
| ferric oxide | $Fe_2O_3$ |
| saccharated ferric oxide | $C_{12}H_{22}Fe_2O_{14}$ |
| ferric sulfate | $Fe_2O_{12}S_3$ |

The ferric nitrate is optionally added at a final concentration of between about 6 mg/L and about 50 mg/L, such as a range of about 26 mg/L to about 50 mg/L, a range of about 40 mg/L to 50 mg/L, and may be added at 40 mg/L, 42.5 mg/L, 45 mg/L, 47.5 mg/L, or 50 mg/L. Other ratios of varying iron or other cations are available, as evidenced by Giles, et al. (Giles, et al., Iron and aluminium based adsorption strategies for removing arsenic from water. J Environmental Management 2011, 92, 3011-3022), and are considered part of the invention. In some variations of the invention, the ferrous salt is hydrolyzed before the salt is added to the sample of water. Accordingly, other Fe salts may be utilizes since the effect will be significantly similar due to the Fe cation changing to form $FeOH_2$ during hydrolysis. In non-limiting examples, the ferrous salt may be hydrolyzed for 12 hours, 24 hours, 48 hours, 60 hours, 72 hours, 96 hours, 100 hours, or over 100 hours before addition to the sample of water.

After the water sat for a time sufficient to permit the ferric salt to interact with the arsenic, a gelling extract obtained from cactus was added to the sample of water. Exemplary concentrations are between about 50 mg/L and about 500 mg/L, such as 50 mg/L, 60 mg/L, 75 mg/L, 90 mg/L, 100 mg/L, 125 mg/L, 150 mg/L, 175 mg/L, 200 mg/L, 250 mg/L, 275 mg/L, 300 mg/L, 350 mg/L, 400 mg/L, 450 mg/L, and 500 mg/L. The sample of water and gelling extract were mixed and allowed to cure, i.e. permitting the arsenic to precipitate out of the sample of water. The gelling extract accelerated precipitate settling within 15 min of addition, achieving 75-99% arsenic removal. As such, the water sample may be cured for 15 minutes or more. For example, the water sample may be cured for 1 hours, 2, hours, 5 hours, 10 hours, 12 hours, 18 hours, or 24 hours. The role of the mucilage was demonstrated by untreated solutions showing no concentration difference and remaining stable for more than 15 days. This mucilage-based technology has the potential to be a relatively inexpensive, environmentally sustainable alternative to synthetic polymer flocculants for removing arsenic from drinking water.

In batch experiments, ferric (Fe(III); $Fe^{3+}$) ions were contacted with arsenate (As(V)) to form a colloidal iron arsenate precipitate, then treated with cactus mucilage in a cylindrical column. The solutions were mixed well and left to stand. After equilibration, sample aliquots were taken from the top and bottom of the column and tested for As and Fe using Hydride Generation Atomic Fluorescence Spectroscopy (HG-AFS) and Inductively Coupled Plasma-Mass Spectrometry (ICPMS). The mucilage accelerated precipitate settling within 15 minutes of addition, coagulating and flocculating the ferric-arsenate complexes. The use of ferric ions and mucilage achieved 85% arsenic removal as indicated by difference in As concentration between the top and bottom of the columns, and better than 90% arsenic removal based on difference between initial and final dissolved As concentration in the column. Arsenic removal is affected by both mucilage concentration and Fe concentration. As concentrations at the air-water interface were higher in experimental solutions than in control (no mucilage). Since mucilage is not a source of As, the only source is by transport of As from the bulk of the solution to the air-water interface. No difference was seen by increasing the concentration of mucilage. However, differences were observed between NE and GE. GE caused a greater average increase in As concentration at the air-water interface, also gave the higher maximum increase.

The role of the mucilage was demonstrated by untreated solutions, composed of $Fe(NO_3)_3$ at concentrations ranging from 5 mg/L to 50 mg/L, As(V) at 100 μg/L and without mucilage, showing no concentration difference and remaining stable to precipitation for more than one week, compared to treated samples, which formed flocs containing the arsenic contaminant. Due to the size of the flocs, the system is able to operate as a direct filtration system with a sand filter. Further, the mucilage may be applied to other systems where solid-liquid separation is desired. Without being bound to any specific theory, the mucilage is thought to assist the precipitation by providing a matrix for stable floc formation, allowing removal of both iron and arsenic simultaneously and providing safe drinking water. This mucilage-based technology has the potential to be a relatively inexpensive, environmentally sustainable alternative to synthetic polymer flocculants for removing arsenic from drinking water. In some embodiments, the pH of the water sample is at between 5 and 6. For example, the pH may be 5.0, 5.1, 5.2, 5.3, 5.4, 5.5, 5.6, 5.7, 5.8, 5.9, or 6.0. Moreover, the treatment compounds, i.e. the ferric salt and mucilage extract, may be removed from the water sample, if desired, by collecting the sample of water after precipitation of arsenic and running the sample of water through a filter, filter cloth, or sand to remove the ferric salt and mucilage.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
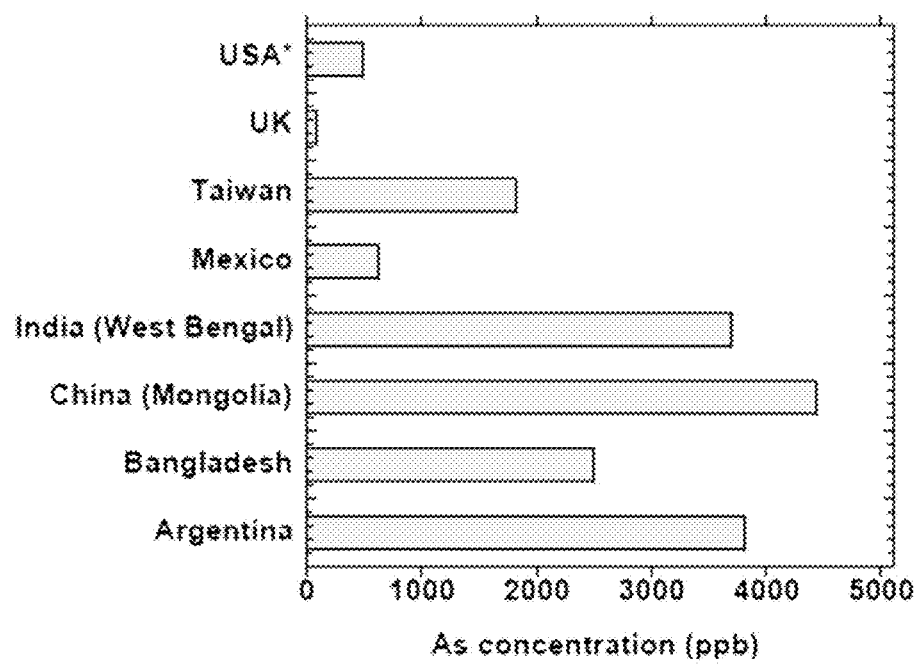
FIG. 1 is a graph showing maximum contaminant levels for arsenic (As) in selected regions of the world.

As used herein, "about" means approximately or nearly and in the context of a numerical value or range set forth means a variation of ±15%, or less, of the numerical value. For example, a value differing by ±14%, ±10%, or ±5% would satisfy the definition of about.

As used herein, "mucilage" is a thick, gluey substance produced by cactus plants, comprising of a composition of glycoproteins and an exopolysaccharides, found in the pads of the cactus plant.

As used herein, "substantially" means largely if not wholly that which is specified but so close that the difference is insignificant.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Mucilage extracts were shown to successfully flocculate the colloidal ferric salt-arsenate solution used as the test solution. Arsenic-contaminated water is first dosed with ferric ions, such as ferric nitrate ($Fe(NO_3)_3$). However, other ferric salts such as ferric chloride and ferric sulfate may also be used. The optimal dosage was found to be 40 mg/L for a challenge water of 100 μg/L arsenic. Cactus mucilage is then added to the water in the form of a suspension; the optimal dosage was found to be 100 mg/L GE. The mixture is then agitated well and left to stand. Within 10 minutes, settling was visible, due to collection/accumulation of precipitate at the bottom of the container. Within 30 minutes, the majority of the settling was complete, though settling was found to continue for up to one week. Higher removal rates were achieved through use of aged ferric solution, rather than fresh, as the aged solution contains more iron hydroxide ($Fe(OH)_3$) on account of hydrolysis, and the $Fe(OH)_3$ is more efficient at arsenic removal than $Fe^{3+}$. The ferric salt hydrolyzed to the rust brown hydrous ferric oxide (HFO) which adsorbed the dissolved arsenate. The mucilage then provided a matrix for the HFO-arsenate complex to accumulate and form dense, strong flocs. The mucilage-HFO-arsenate complex settled rapidly thereby removing the arsenic from solution. With this process, 75-99% arsenic removal has been achieved. In the absence of mucilage, the colloidal precipitate was stable for at least 15 days.

Although the mucilage has a direct interaction with As, the extent of removal is modest, which peaked at 35% removal. For this reason, Fe(III) salts were used to strongly bind and precipitate the As prior to removal by mucilage.

Example 1

Fresh cactus pads (*Opuntia ficus-indica*) were obtained from a nursery in Tampa, Fla., USA obtained originally from Living Stones Nursery, Tucson Ark. All chemicals used were analytical grade or better and purchased from Fisher Scientific (Pittsburgh, Pa.).

Mucilage was extracted from the fresh cactus pads as a gelling extract (GE) and a non-gelling extract (NE). The pads were washed, dried and weighed. The pads were diced or peeled and boiled for 20 min, then the mixture was liquidized in a blender (Osterizer™, Sunbeam Products, Inc., Boca Raton, Fla.). 1M sodium hydroxide (NaOH) was added to neutralize the mixture and then centrifuged to separate the supernatant, which contains the NE, from the solid precipitate, containing the GE. Before the GE was extracted, the non-gelling extract (NE) was removed. The GE was then extracted using an adaptation of a method developed by Turquois et al. (Turquois, et al. Extraction of highly gelling pectic substances from sugar beet pulp and potato pulp: influence of extrinsic parameters on their gelling properties. *Food Hydrocolloids* 1999, 13, (3), 255-262). The solids were mixed with 7.5 g/L sodium hexametaphosphate [$(NaPO_3)_6$] in 50 mM NaOH, in a 1:1 mass-to-volume ratio of solids to solution. The mixture was stirred for 1 h, then vacuum filtered with knitted polyester cloth (Polx 1200, Berkshire Corp., Great Barrington, Mass.) or to obtain the filtrate. The filtrate pH was lowered to 2 using hydrochloric acid (HCl) and refrigerated overnight (~5° C.) in order to precipitate the GE. The precipitate was separated by centrifugation, re-suspended in sufficient deionized (DI) water to cover the pellet, and the pH adjusted to 8.0 with 1M NaOH to re-dissolve the precipitate. The resulting solution was purified by successive filtering through a 1.2 μm and a 0.45 μm membrane. The GE was re-precipitated with acetone or isopropanol in a 2:3 liquid-to-solvent volume-to-volume ratio, then washed with alcohol and dried under ambient conditions.

The non-gelling extract (NE) was collected as described above, and sodium chloride added to the supernatant to form a final concentration of 1M NaCl. The supernatant was filtered with knitted polyester cloth (Polx 1200, Berkshire Corp., Great Barrington, Mass.) or Whatman 41 filter paper, based on the viscosity of the liquid, to obtain the filtrate. Acetone or isopropanol was added in a 2:3 volume-to-volume ratio of supernatant to solvent to precipitate the NE. The precipitate was washed with ethanol-water mixtures in a graded series (70%, 80%, 90%, 95% ethanol, and absolute ethanol) to remove any remaining impurities. The precipitate was left to dry at room temperature overnight, followed by an overnight drying in an air oven (Yamato DX-41, Japan).

Example 2

Mucilage was alternatively extracted from the fresh cactus pads described in Example 1 as a non-gelling extract (NE). Cactus pads were washed, dried and weighed, and cut longitudinally in halves. The parenchyma (white fleshy inside) of the pads was scooped out with a spoon and pressed through a potato press to crush the parenchyma and break the mucilaginous cells thereby releasing the mucilage. Alternatively, the crushing of mucilaginous cells may be achieved with other tools, such as crushing the material with a stone or mortar and pestle.

The pressed liquid was collected and the solids were discarded. Isopropanol was added to the liquid in a volume-to-volume ratio of 3:2 alcohol to precipitate the mucilage. The precipitate was washed with three 5 mL to 10 mL aliquots of isopropanol. The precipitate was placed on a petri dish to dry overnight then it was oven dried at 50° C. overnight. The dry precipitate was then pulverized with a mortar and pestle and stored in an airtight plastic vial.

Example 3

Mucilage was alternatively extracted from the fresh cactus pads described in Example 1 as a non-gelling extract (NE). Cactus pads were washed, dried, weighed and diced into approximately 1 cm cubes. The cactus cubes were then immersed in 1% sodium chloride solution in a 1:1 mass to volume ratio. Liquid was added to the material until the solution covered the diced cactus. The mixture was boiled for 15 minutes then cooled. The liquid and solids were squeezed through a potato press and the liquid was retained while the residual solids were discarded. Isopropanol was added to the liquid in a 3:2 alcohol to liquid volume-to-volume ratio to precipitate the mucilage. The precipitate was washed with three 5 to 10 mL aliquots of isopropanol. The precipitate was placed on a petri dish to dry overnight then it was oven dried at 50° C. overnight. The dry precipitate was then pulverized with a mortar and pestle and stored in an airtight plastic vial.

Example 4

The GE and NE were analyzed to determine the composition and [physical characteristics of the two extracts.

Figure 2:
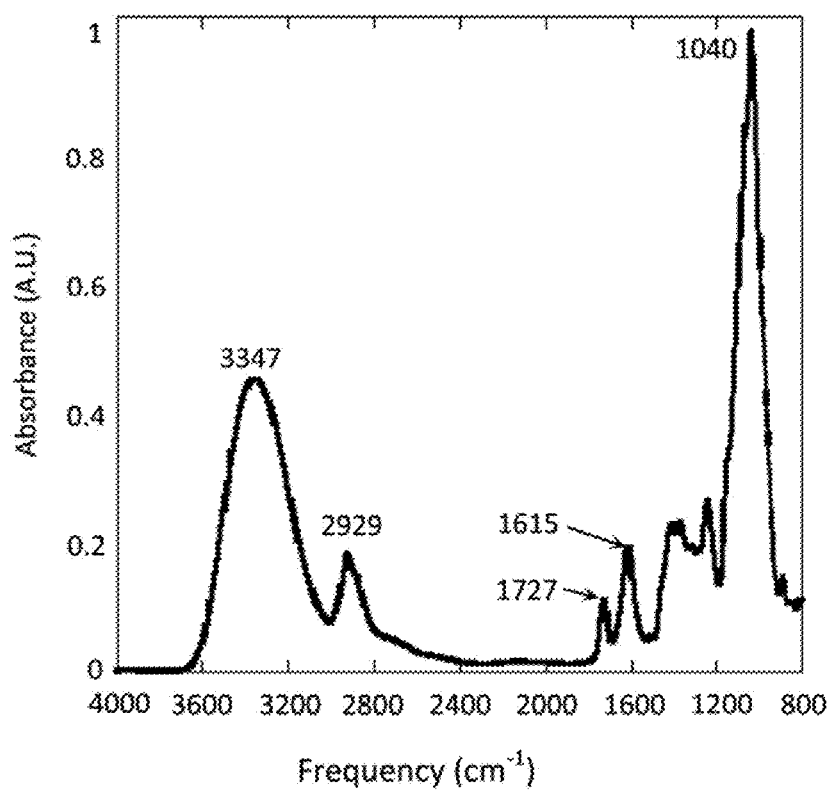
FIG. 2 is an ATR-FTIR spectrum of native Non-gelling Extract (NE) showing the major absorption bands. The labeled bands correspond to OH (3350 cm-1), CH (2937 cm-1), COO— (1609 cm-1, 1416 cm-1), COC (1250 cm-1) and CO from secondary alcohol (1100 cm-1) groups.
Figure 3:
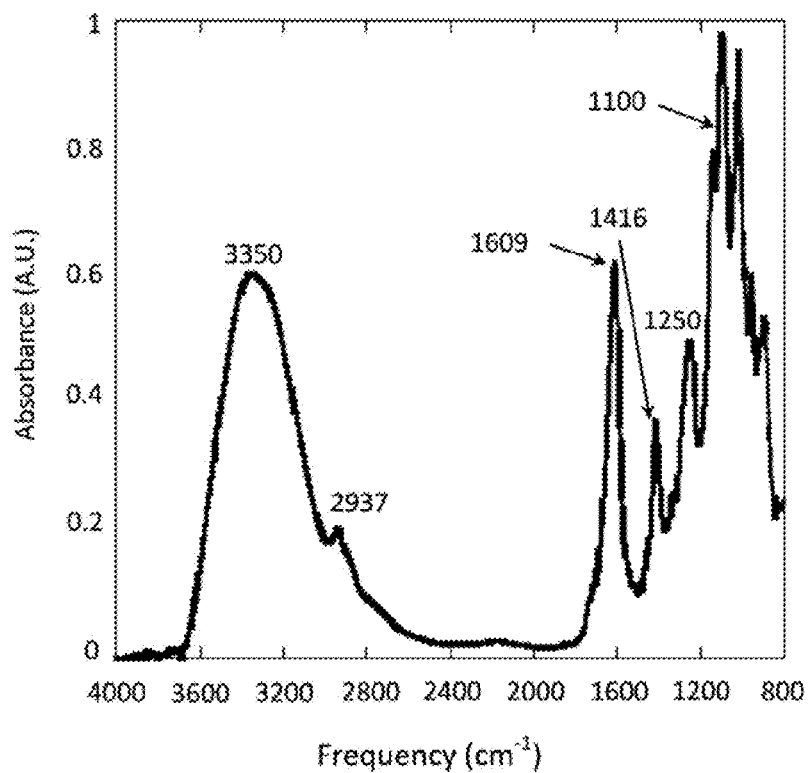
FIG. 3 is an ATR-FTIR spectrum of native Gelling Extract (GE) showing the major absorption bands. The labeled bands correspond to OH (3347 cm-1), CH (2929 cm-1), CO (1727 cm-1, 1615 cm-1) and CHOH (1041 cm-1) groups In FTIR absorbance spectroscopy, peak shifts and intensity changes are important for inferring chemical interaction. Peak shifts signify a change in the chemical environment of a functional group. The coupled appearance and disappearance of absorption bands indicate a reaction involving the corresponding functional group.

The ATR-FTIR spectra of both the gelling extract (GE) and non-gelling extract (NE) show the characteristics of pectic polysaccharides, as seen in FIGS. 2 and 3, but differ primarily due to the higher uronic acid content of GE. Pectins have a D-galacturonic acid backbone and various degrees of branching composed of neutral sugars, and methylation of the carboxylic acid functional group. Their spectra show the functionalities associated with the carboxylic acid and carboxylate, ether and alcohol groups that comprise these compounds.

In the GE spectrum, there are four main features: the first is the broad band at 3350 $cm^{-1}$ which corresponds to OH stretching of alcohol and carboxylic acid —OH groups involved in intermolecular hydrogen bonding. The second is two bands at 1609 $cm^{-1}$ and 1416 $cm^{-1}$ corresponding to the antisymmetric and symmetric COO— stretch characteristic of carboxylic acid salts. Thirdly, the bands at 1250 $cm^{-1}$ and 1140 $cm^{-1}$ correspond to C—O—C ether stretch. Lastly, two strong bands at 1140 $cm^{-1}$ and 1100 $cm^{-1}$ are due to C—O stretch of secondary alcohols and C—O—H stretch in cyclic alcohols, respectively. Significant similarities exist between the spectra of GE and NE; however, four notable differences distinguish NE from GE. A more pronounced band is observed at 2929 $cm^{-1}$ for the CH stretching. Further, NE shows the expected carbonyl C=O stretch at 1727 $cm^{-1}$ that is absent in GE. The most intense band for NE occurs at 1041 $cm^{-1}$ due to HC—O—H stretch of cyclic alcohols. The most notable difference between the two extracts is seen in the region 1250 $cm^{-1}$ to 850 $cm^{-1}$. Coimbra, et al. showed that the intensity of the bands at 1100 $cm^{-1}$ and 1018 $cm^{-1}$ correlated with the uronic acid content of pectic polysaccharides; on this basis GE is deduced to have a higher uronic acid content than NE (Coimbra, M., A. Barros, et al. (1998). "Multivariate analysis of uronic acid and neutral sugars in whole pectic samples by FTIR." Carbohydrate Polymers 37: 241-248.).

TABLE 3

Functional groups assigned to major bands in spectra of gelling (GE) and

| Functional groups | Gelling extract (GE) ($cm^{-1}$) | Non-gelling extract (NE) ($cm^{-1}$) |
|---|---|---|
| Hydrogen bonded O—H from alcohol and carboxylic acid groups | 3350 | 3347 |
| CH groups from aliphatic backbone | 2937 | 2929 |
| Carbonyl group (C=O) from carboxylic acid | | 1727 |
| Carboxyl group from carboxylic acid/carboxylate | 1609 1416-1331 | 1615 1411-1317 |
| Ether groups (C—O—C) | 1250 1140 | 1245 |
| C—O from 2d alcohol, CHOH from cyclic alcohol | 1100, 1019 | |
| Indicative of uronic acid content CHOH of cyclic alcohols | | 1041 |

The carbohydrate composition of the GE and NE was performed using a modified version of the NREL LAP (NREL (2008). Determination of Structural Carbohydrates and Lignin in Biomass Laboratory Analytical Procedure (LAP). Golden, National Renewable Energy Laboratory). The modifications were that the experiment was scaled to ⅕ of the suggested masses and volumes, and the 4% acid hydrolysis took place in the reactor tubes in the sand bath instead of the autoclave.

The sugars composition by mass of GE and NE is shown in Table 5.1 below. NE has a higher percentage by mass of neutral sugars than GE. The most abundant sugar for NE is arabinose while that of GE is glucose. Rhamnose was not detected herein, but it was reported in the literature, while glucose was detected here but not reported in the literature. Cardenas et al. reported the composition of the cactus pectin as 85.4% uronic acids, 7.0% galactose, 6.0% arabinose and minor quantities of rhamnose and xylose (Cardenas and Goycoolea, et al. (2008). "On the gelling behaviour of 'nopal' (*Opuntia ficus indica*) low methoxyl pectin." Carbohydrate Polymers 73(2): 212-222). Compared to the literature, the formed extracts (GE and NE) show a higher neutral sugar content and, as with NE, the apparent substitution of rhamnose with glucose.

TABLE 4

Sugars composition by mass (%) of GE and NE mucilage extracts.

| | Composition by mass (%) | |
|---|---|---|
| Sugars | Gelling Extract (GE) | Non-gelling Extract (NE) |
| glucose | 9.89 | 1.03 |
| xylose | 3.95 | 10.80 |
| galactose | 7.35 | 14.66 |
| arabinose | 8.90 | 24.38 |
| total | 30.10 | 50.86 |

The inorganic element composition of the mucilage extracts was determined by Laser-Induced Breakdown Spectroscopy (LIBS) using a LIBS2500plus spectrometer (Ocean Optics, Inc., Dunedin, Fla.). The experimental set-up consisted of a 200 MJ Q-switched 1064 nm Nd:YAG pulsed laser (Quantel, Les Ulis, France) S-GIANT, with a laser pulse duration of 10 ns. The laser was focused on a stationary target in an enclosed eyewear-safe sample chamber (LIBS-SC, Ocean Optics, Inc.). The samples were mounted on a manually controlled x-y stage, in an inert gas atmosphere. The detection system consisted of seven high-resolution miniature fiber optic spectrometers with 2048-element linear charge-coupled device (CCD) array. The data was displayed using OOILIBS software (Ocean Optics, Inc.).

Figure 4:
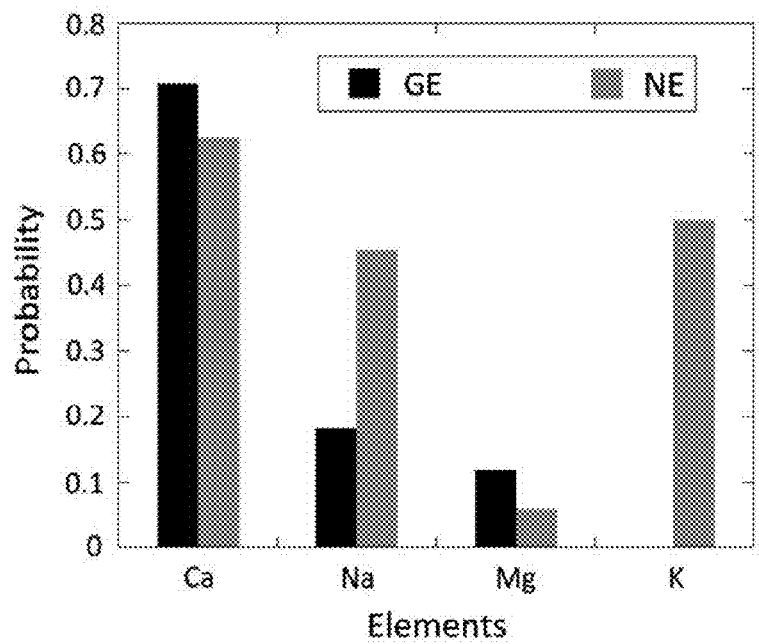
FIG. 4 is a graph showing the major inorganic elements in extracts of cactus mucilage.

The GE and NE powders were pressed into pellets and laser pulses were focused on the surface of the pellets. The high temperature of the laser formed a microplasma of the sample which, as it cooled, emitted the characteristic wavelengths of the comprising elements. Qualitative data were collected from these experiments, as seen in FIG. 4. The maximum lines in GE, as well as NE, were for calcium (Ca). GE also showed significant lines for sodium (Na) and magnesium (Mg). Apart from Ca, NE showed significant lines for Na and potassium (K).

Mucilage structure and physical characteristics were analyzed using transmission electron microscope (TEM) imaging. Samples (100 mg) of mucilage were suspended in 50 mL DI water to make a stock of 2000 mg/L suspension and the stock solutions diluted to the desired concentration, between 5 mg/L and 500 mg/L. Approximately 20 μL of sample was mounted on a formvar (polyvinyl formal) coated copper TEM grid, stabilized with evaporated carbon film (Electron Microscopy Sciences, Hatfield Pa.) and allowed to air dry. The dry samples were stained with 1% uranyl acetate; approximated 20 μL of 1% uranyl acetate was pipetted unto the sample and allowed to air dry. The electron microscope used was a Morgagni 268 (FEI Co., Hillsboro Oreg.). The images were observed at an accelerating voltage of 60 kV.

GE has a lace-like network with significant separation, seen as spaces, between the polymer strands while NE has a much denser packing, with smaller spaces, like a fishing net. The lace-like structure arrangement of GE suggests conformational restrictions imposed by an orderly arrangement of a repeating monomer; steric hindrances may dictate the closeness of approach of polymer strands. This may be a result of the typical structure of pectins having linear or "smooth" α-D-galacturonic acid backbone supporting neutral sugar residues branches referred to as "hairy" regions (Schols and Voragen (2002). The chemical structure of pectins. Pectins and their manipulation. G. B. Seymour and J. P. Knox. Boca Raton: Fla., CRC Press). The branches may impede the how closely the linear regions can align. By contrast, the smooth featureless appearance of NE suggests an undifferentiated, random arrangement of the heteropolysaccharide polymers with no restrictions on aggregation.

The extracts were also tested using surface tensiometry in water at the air-water interface by the du Noüy ring method using a Sigma 701 force tensiometer (KSV Instruments Ltd, Finland) and a 0.37 mm wire diameter, 60 mm circumference platinum-iridium ring. The temperature was 20° C. The instrument was calibrated before each set of experiments against freshly drawn samples of Milli-Q water. Samples of mucilage (both GE and NE) suspended in water with concentrations ranging from 500 to 3000 mg/L were prepared. Sample volume was 25 mL. Between the measurement runs, the ring was cleaned with acetone, isopropanol, ethanol and ultra-pure water then dried in a stream of nitrogen. Surface tension data were recorded as the average values of 1,000 measurements and were automatically corrected using Huh and Mason formula (Huh and Mason (1975). "A rigorous theory of ring tensiometry." Colloid Polymer Science 253: 566-580).

Figure 5:
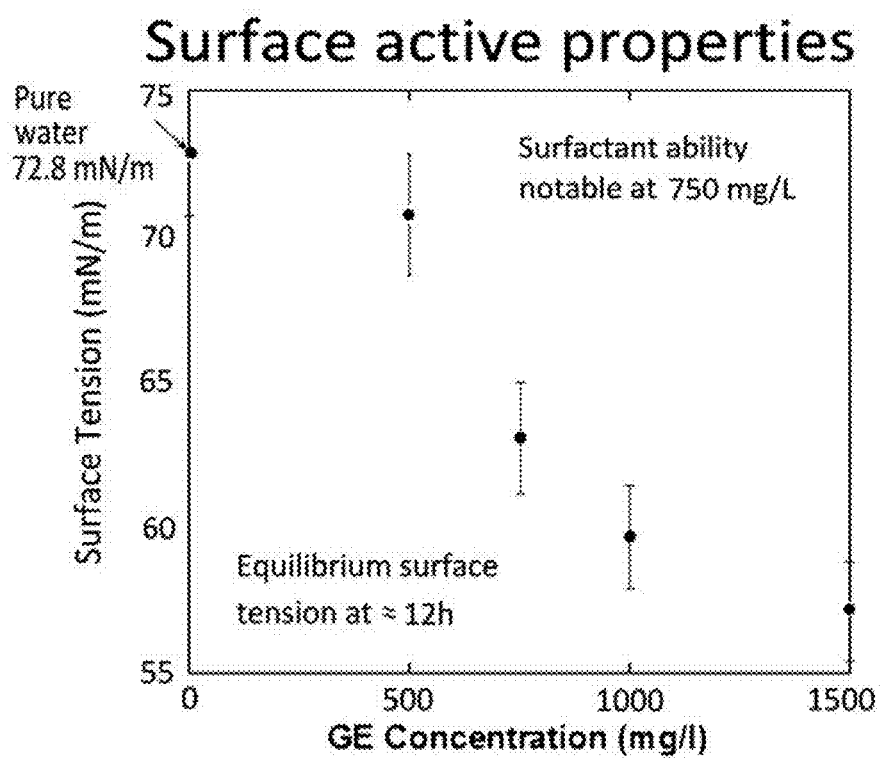
FIG. 5 is a graph showing the surface tension of water upon addition of GE mucilage extract.

The decrease in surface tension increased with mucilage concentration. However, no change was noted at concentrations below 750 mg/L. A maximum surface tension decrease of 30% was observed with GE but only 16% was observed for NE, as seen in FIG. 5. The lowering of surface tension is characteristic of amphiphilic molecules and is accounted for by migration of the solute molecules to the air-water interface (van Oss (2006). Interfacial forces in aqueous media. Boca Raton, CRC Press). It should be noted however, that the concentrations used to effect the surface tension lowering are much higher than those employed to interact with As.

Example 5

Next, the mucilage and ferric salt was tested to determine As removal. Two types of control experiments were run; As(V) solutions without mucilage, and mucilage solutions without As(V), with all other test conditions and concentrations kept constant. The As(V) stock solution used in the experiments was prepared by dissolving solid sodium arsenate in sufficient de-ionized (DI) water to bring the final concentration to 1000 μg/L. The stock solution was continuously aerated using an aquarium aerator which maintained the dissolved arsenic in the oxidized arsenate form. pH was adjusted using sodium hydroxide and hydrochloric acid.

The stock solution was continuously aerated using an aquarium aerator, which maintained the dissolved arsenic in the oxidized arsenate form. This was done to represent the natural aeration of groundwater when pumped above ground. As needed, pH was adjusted using sodium hydroxide and hydrochloric acid. 10 mL of 100 μg/L As(V) solutions were treated with ferric nitrate ($Fe(NO_3)_3 \cdot 9H_2O$), followed by GE mucilage to attain final Fe(III) concentrations of 6-50 mg/L and final mucilage concentrations of 20-500 mg/L. The solutions were thoroughly mixed then left to stand.

Final As(V) solutions, 10 mL of 60 μg/L to 100 μg/L As, were treated with GE and NE to attain final mucilage concentrations of 5 mg/L to 100 mg/L in 15 mL centrifuge tubes. After 24 to 36 hours of equilibration, 1 mL sample aliquots were removed from the air-water interface and the total As concentration was determined by Hydride Generation-Atomic Fluorescence Spectroscopy (HG-AFS) and Inductively Coupled Plasma-Mass Spectrometry (ICP-MS). Total arsenic As concentrations were measured on a PSA 10.055 Millennium Excalibur HG-AFS spectrometer. ICP-MS analysis for total arsenic was carried out using a Perkin Elmer ELAN DRC ICP-MS spectrometer equipped with an autosampler. $^{75}$As mass was measured in three replicates. Arsenic calibration solutions (0, 0.5, 1, 5, 10 and 20 μg/L) were run before each sample series. In-between drift monitor checks were performed after each 10-15 samples. Arsenic concentrations in unknown solutions were calculated based on an external calibration curve and error was determined based on the external standard NIST 1064a. Several controls were run: As(V) only, Fe(III) only, mucilage only, Fe(III) and As(V), Fe(III) and mucilage and, As(V) and mucilage solutions. All tests were run in triplicate at room temperature and ambient conditions. Kinetic trials were run using timed batch experiments for intervals between 5 min to 1 week.

Figure 6:
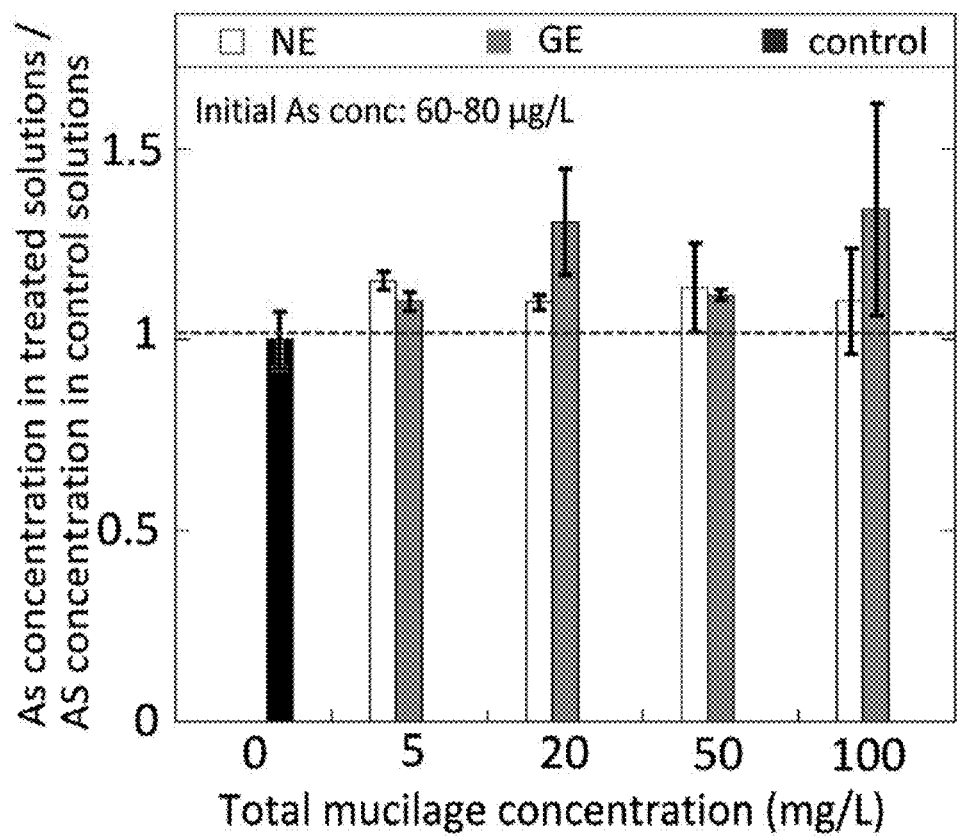
FIG. 6 is a graph showing As concentrations at air-water interface of mucilage-treated solutions relative to untreated control solutions as a function of mucilage extract and concentration (pH 5.5).

Both GE- and NE-treated solutions showed higher concentrations of As at the air-water interface than the control solution, shown in FIG. 6. With conventional sorbents, the concentration of the adsorbate in solution decreases and this decrease is directly related to the removal of the adsorbate. A different scenario was observed with the mucilage; As concentrations increased at the air-water interface as a consequence of mucilage binding and transporting it to this region. Hence, the removal was correlated with this increase in concentration. Results were reported in terms of increase in As concentration (at the air-water interface), calculated according to:

$$\text{percent increase} = \frac{\text{test solution concentration} - \text{control solution concentration}}{\text{control solution concentration}} \times 100\% \quad (I)$$

Statistical analysis of variance was done using Student's t test with $\alpha=0.1$ to seek significant difference between mucilage-treated solutions and untreated controls. Variations on the batch tests included the addition of calcium ($ca^{2+}$) ions to the test solutions and, in separate experiments, the use of groundwater instead of DI water as the solution matrix. Surrogate groundwater samples were collected from a public drinking fountain in Tampa, Fla., and spiked with As to form a 10 mL final volume solutions of 100 µg/L As(V). The As-spike water was then dosed with iron (III) nitrate ($Fe(NO_3)_3$) solution and GE mucilage. The $Fe(NO_3)_3$ concentration ranged from 0 to 50 mg/L while the mucilage concentration ranged from 0 to 500 mg/L. After equilibration, sample aliquots were taken from the top and bottom of the columns and the concentrations of both iron (Fe) and As were determined by ICP-MS.

Samples of water taken from the treated columns was vaporized by a high speed flow of argon creating a mist of analyte and argon. The mist was then passed to an RF coil and ignited to about 7000 K to 10000 K, and the plasma ions directed to a mass spectrometer under vacuum to differentiate and quantify the ions based on their mass-to-charge ratio.

Figure 7:
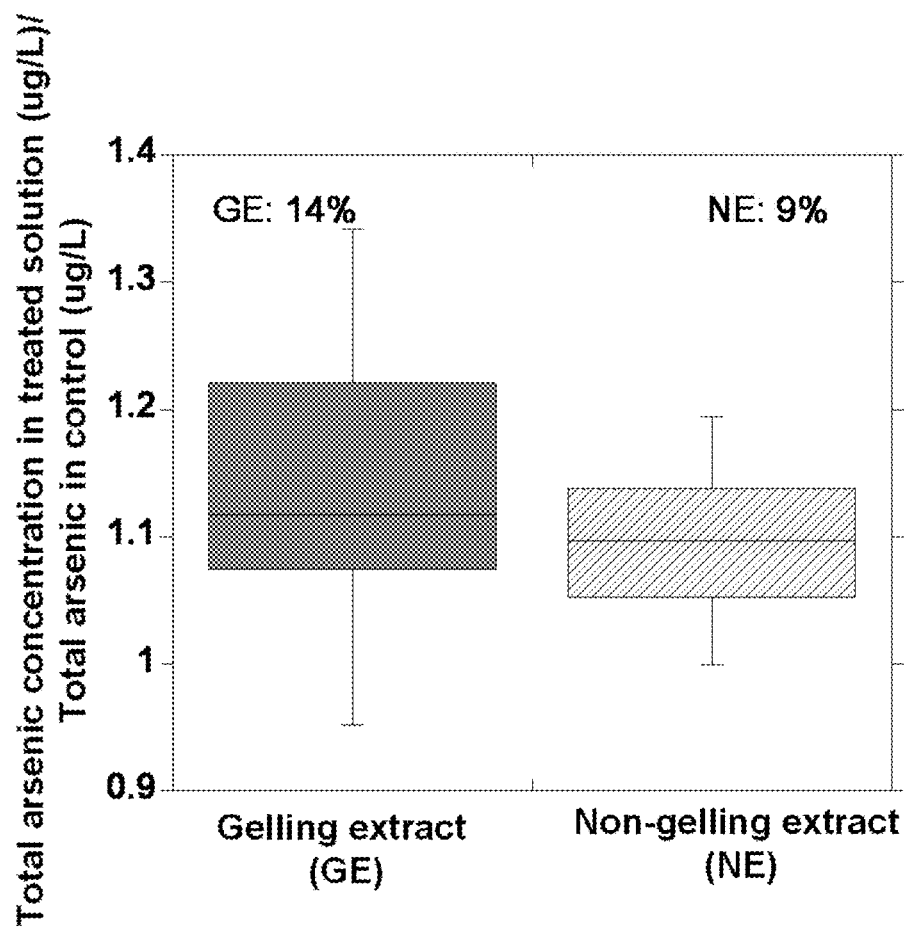
FIG. 7 is a graph showing GE mucilage extracts caused a greater average increase in As concentration at the air-water interface and an increase in flocs as precipitates at the bottom of the solution.
Figure 8:
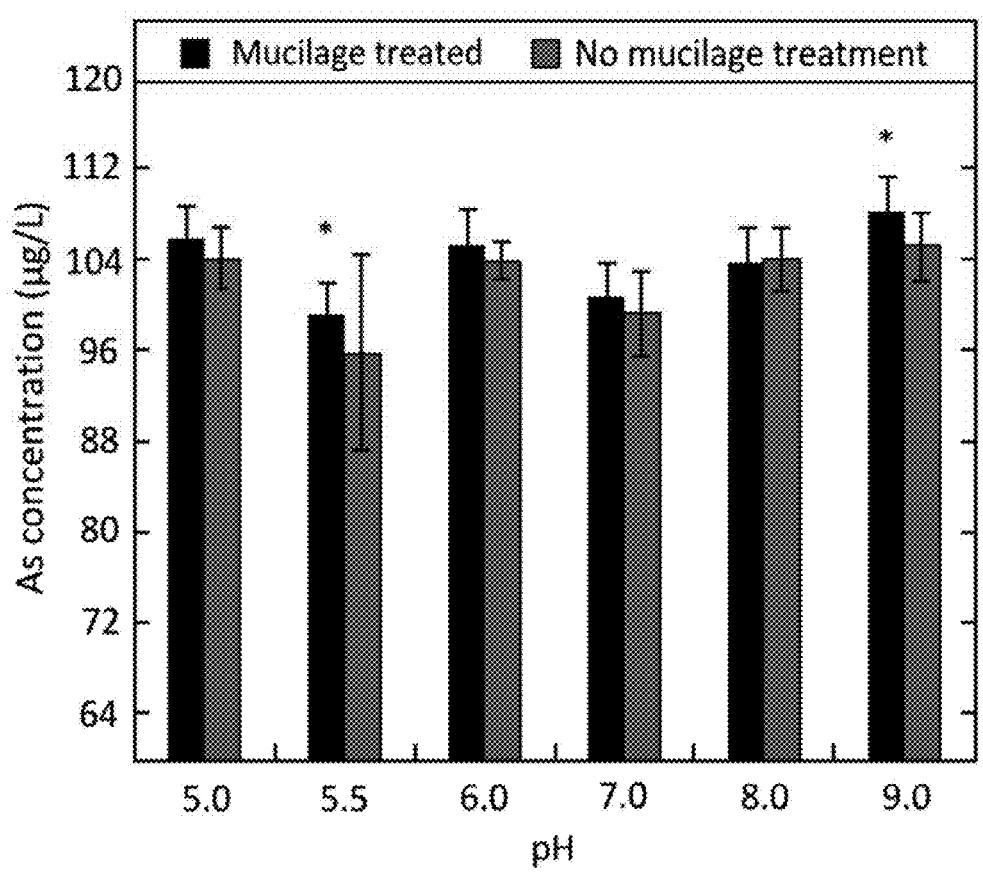
FIG. 8 is a graph showing As concentrations at the air-water interface of mucilage-treated solutions (GE) relative to untreated control solutions as a function of initial solution pH. Significant difference ($\alpha=0.1$) between control and treatment is indicated by (*).

The GE showed an average 14% increase in As concentration at the air-water interface, while the NE showed an average 9% increase, as seen in FIG. 7. GE showed a wider response range and higher maximum increase of 34% than NE, which had a maximum increase of 17%, indicating that the increase in concentration is extract dependent. GE was consequently chosen as the more reactive/responsive extract.

On a mass basis, the 34% maximum increase of As concentration shown by GE converts to 34 μg arsenic (approximately 4%) transported from the bulk solution to 1 mL solution at the air-water interface. These results present an unexplored interaction between pectic polysaccharides and metal oxyanions. Since the mucilage is not a source of As, the increase of As concentration at the air-water interface directly shows an interaction with As, and As transportation by the mucilage.

Pectins have been extensively shown to interact with metal cations. Without being bound to any particular theory, the transport of the arsenic to the air-water interface is thought to occur due to an increase in the hydrophobicity of the mucilage. The proposed mechanism is that the amphiphilic mucilage binds to the As(V) ions by using its ionizable hydroxyl, carboxyl and carbonyl groups. Normally these ionizable groups are used to stabilize the mucilage in the bulk of the aqueous solution by attracting counter ions. On interaction with As, the groups are no longer available, becoming destabilized and more hydrophobic, repelling the mucilage-As complex to the air-water interface.

It was noted that the observed increase in As concentration at the air-water interface was independent of the mucilage concentration, though both extracts showed considerable variation in performance. Without being bound to any particular theory, one probable reason for the lack of response to increasing mucilage concentration is that at higher concentrations, the mucilage tends to aggregate and form larger molecular ensembles (Cardenas, et al (1997). "Rheology and aggregation of cactus (*Opuntia ficus-indica*) mucilage in solution." Journal of the Professional Association for Cactus Development 2: 152-159). Aggregation may be hindering the mucilage's interaction with the As(V) ions. Further, the implication is that lower concentrations of both GE and NE may be more effective at transporting As(V) ions to the air-water interface, which will result in lower water treatment costs if mucilage technology is used.

Three batch trials were run in triplicate or better at pH 5, 5.5, 6, 7, 8 and 9 to investigate the effect of pH on the interaction between mucilage and arsenic, without any ferric ions. These pH values were chosen to reflect the pH of natural waters. There are two reasons why pH is expected to be an important variable or factor in the interaction in the system. Firstly, pH affects protonation of arsenate in solution which in turn affects the charge on the oxyanion. In the pH range of natural waters, the dominant arsenate species are $H_2AsO_4^-$ (pKa, 1=2.91) and $HAsO_4^{2-}$ (pKa, 2=6.94). Secondly, pH not only affects the protonation and charge on the mucilage but also the conformation. Note that pH 5.5 is the initial solution pH. GE was chosen for pH trials on account of its better interaction with As(V) ions than NE. The initial As concentration was 100 μg/L (as in the previous experiments) and the GE concentration used was 50 mg/L.

As shown in FIG. 8, only at pH 5.5 and 9, were small but statistically significant differences observed between mucilage-treated solutions and non-mucilage treated controls. Further significant difference was observed between the mucilage-treated solutions at these two pH levels. These results indicate that solution pH does affect the interaction between the GE and arsenate and further, gives insight into the nature of the interaction. GE, an anionic polyelectrolyte, becomes increasingly negatively charged with increasing pH due to ionization of —OH groups from alcoholic and carboxylic groups (Cardenas, et al (1997). "Rheology and aggregation of cactus (*Opuntia ficus-indica*) mucilage in solution." Journal of the Professional Association for Cactus Development 2: 152-159; Medina-Torres, et AL. (2000). "Rheological properties of the mucilage gum (*Opuntia ficus indica*)." Food Hydrocolloids 14: 417-424; Cardenas, et al. (2008). "On the gelling behaviour of 'nopal' (*Opuntia ficus indica*) low methoxyl pectin." Carbohydrate Polymers 73(2): 212-222).

The As (V) oxyanion is polyprotic and changes protonation level with pH. In weakly acidic conditions such as pH 5.5 it exists as dihydrogen arsenate $H_2AsO_4^-$, while in weakly basic conditions (such as pH 9) it exists as hydrogen arsenate $HAsO_4^{2-}$ (Benjamin (2002). Water Chemistry. Illinois, Waveland Press). Our proposed mechanism of interaction is via hydrogen bonded bridging between the protons associated with the As species and the ionized carbonyl and carboxyl groups on the mucilage. It appears that there is a compensation between less ionized groups on the mucilage at lower pH with the higher number on protons on the $H_2AsO_4^-$ to make the interaction comparable to the higher pH scenario where the mucilage is more ionized but the arsenate has less protons. The activity in these pH regions versus the lack of activity from pH 6 to 8 may be due to poorer charge transfer as the pH is in the neutral region. The mucilage is therefore expected to perform better in solutions with higher ionic strength to facilitate charge transfer.

The Total Organic Carbon (TOC) of the solutions was analyzed to determine the distribution of the mucilage in the solutions in order to definitively link the mucilage to the transport of As to the air-water interface. Ten mL samples of 100 μg/L As were treated with 50 mg/L GE in 15 mL centrifuge tubes. Sample aliquots were taken from the top and bottom of the tubes for TOC determination. An automatic pipette was used to remove the sample from the top of the tube then a 1 mL transfer test pipette was inserted into the tube to remove a sample from the bottom. The TOC of the bulk solution was calculated as the difference between TOC of the entire solution and that of the top and bottom combined. TOC was measured using a TOC analyzer TOC-V equipped with an automatic sample injector (Shimadzu Corp., Kyoto, Japan). Potassium hydrogen phthalate standard solution was used for calibration of the system. The TOC detection limit was 50 μg/L.

Figure 9:
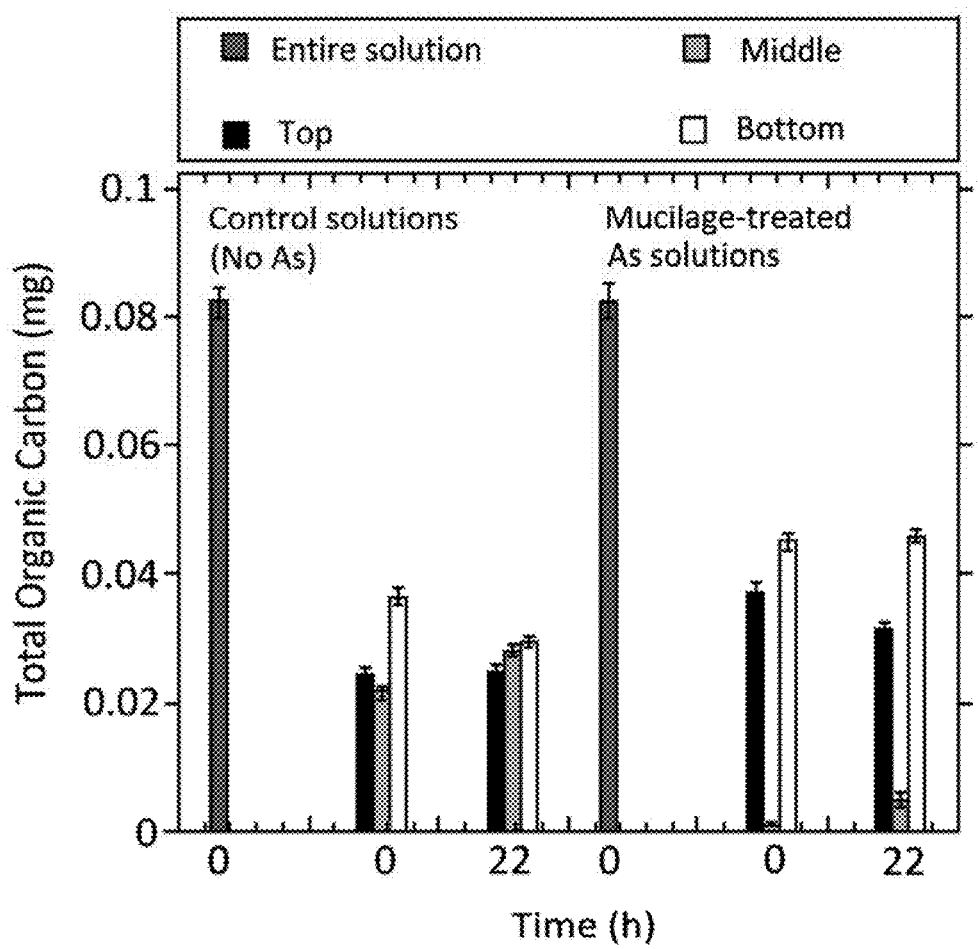
FIG. 9 is a graph showing mass distribution of mucilage (reported as Total Organic Carbon) in solution.
Figure 10:
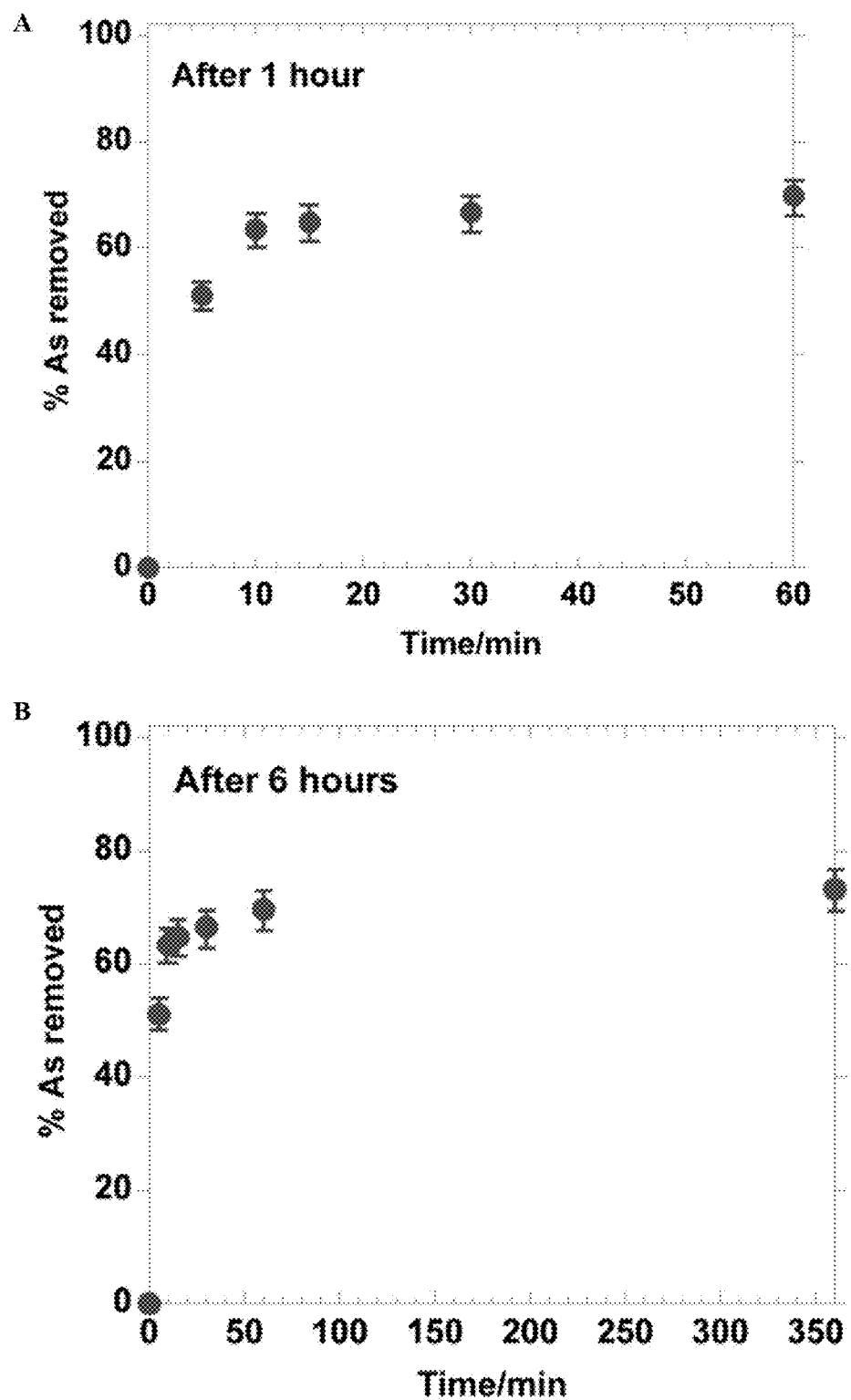
FIGS. 10(a) and (b) are graphs showing kinetics of iron-mucilage system at (a) one hour, and (b) 6 hours. Within 15 min the system reaches equilibrium that is stable up to 24 h.
Figure 11:
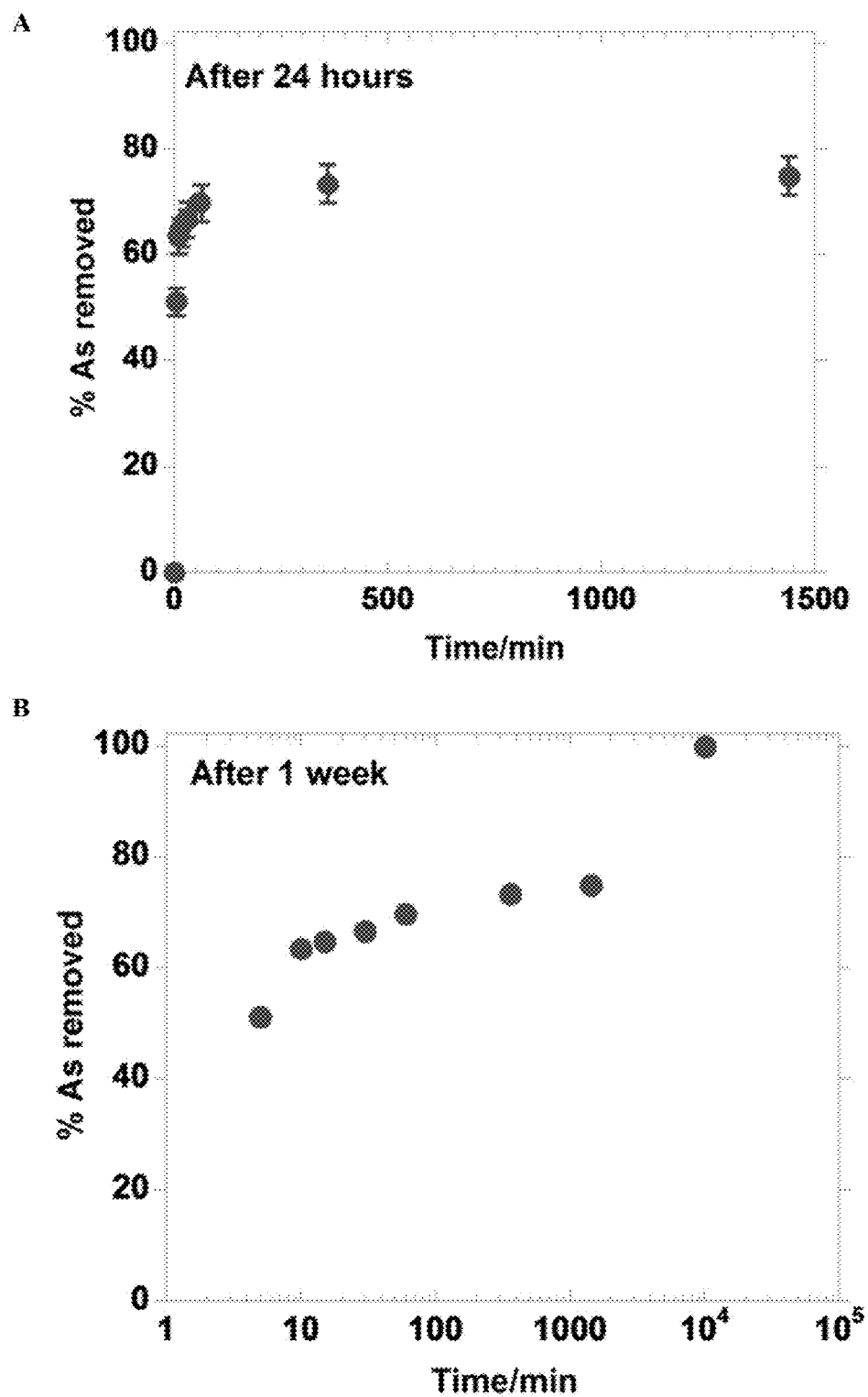
FIGS. 11(a) and (b) are graphs showing kinetics of iron-mucilage system at (a) 24 h and (b) one week from the time of mucilage addition. As solutions were prepared, dosed with Fe solution, and left overnight. The mucilage was added, mixed thoroughly, allowed to stand for a predetermined time, and aliquots removed for testing. Within 15 min the system reaches equilibrium that is stable up to 24 h.

The TOC in the bulk solution was determined by subtracting the TOO of the combined top and bottom of the solution from that of the entire solution. As shown in FIG. 9, the TOC concentration in the entire solution, which correlates to the total mucilage concentration, does not change on addition of As. However, the distribution of mucilage in the solution does change in the presence of As, with a larger proportion of TOC in the bulk of the control solutions than in the mucilage-treated As solutions, indicating that mucilage migrated from the bulk of the solution primarily to the air-water interface due to the presence of As.

Example 6

The strong affinity of iron) ($Fe^0$) and iron oxides and hydroxides for As is well-known. Iron oxides and hydroxides form strong complexes with arsenic oxyanions in a number of reactions (Dixit and Hering (2003). "Comparison of Arsenic(V) and Arsenic(III) Sorption onto Iron Oxide Minerals: Implications for Arsenic Mobility." Environmental Science & Technology 37(18): 4182-4189). One challenge to scaling down these systems for household use is the length of time and large volume reactor required for sedimentation. In this study, the flocculant properties of the mucilage were exploited to improve the efficiency of a bench scale coagulation-flocculation treatment by removing the need for prolonged sedimentation. As solutions were mixed with iron nitrate ($Fe(NO_3)_3$) and mucilage.

In order to study the kinetics of the system, batch experiments were run. Solutions of As were treated with Fe(III) salt (50 mg/L) and 100 mg/L mucilage, stirred, then sampled at the end of different time intervals. The amount of As removed by the mucilage over time increased for the optimized initial conditions of 50 mg/L Fe, 100 mg/L mucilage and As challenge of 100 μg/L, as seen in FIGS. 10(a) through 11(b). The effect of adding cactus mucilage to solutions with iron (Fe) salt and As was easily visible as flocs formed immediately after mixing and standing. The process achieved visual separation within 10 minutes with the majority of the removal being achieved in 30 minutes. Three processes made this possible; the hydrolysis of the Fe salt to iron hydroxide and oxyhydroxide in situ, the strong binding of the arsenate by the iron hydroxide and oxyhydroxides to form solid precipitates, and the coagulation of the precipitates to form flocs large enough to settle out of solution. The mucilage enhanced the coagulation and flocculation of the precipitates.

Figure 12:
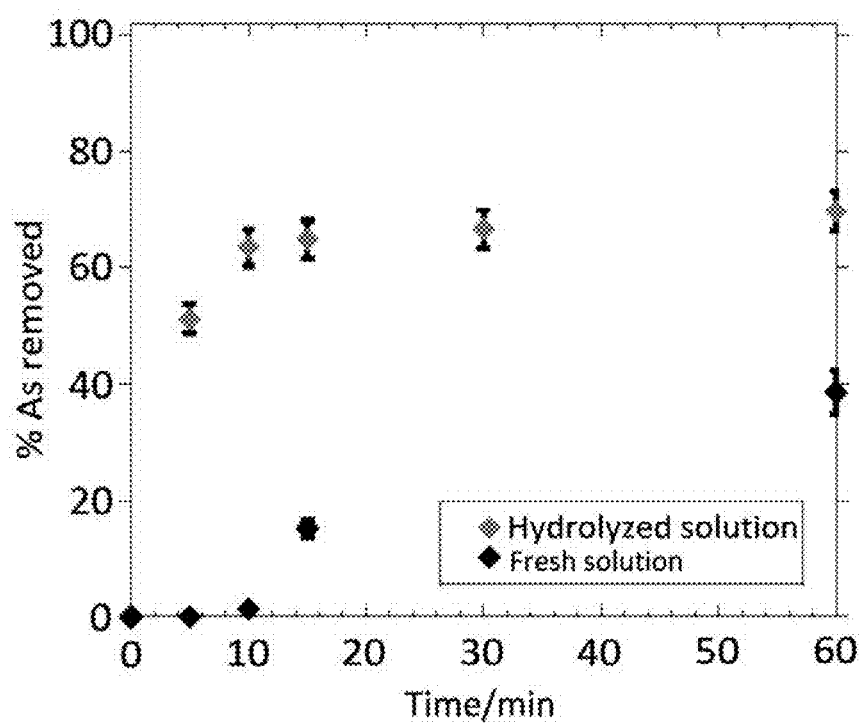
FIG. 12 is a graph showing removal of As as a function of Fe hydrolysis. Hydrolysed Fe solution gave higher removal at 24 h. Initial As concentration: 100 μg/L; GE concentration: 100 mg/L; initial pH: 6.5.

With prolonged settling times, higher removal extent were achieved. The extent of removal depended on the extent of hydrolysis of the Fe (III) solution to hydrous ferric oxides in situ, the strong binding of the arsenate by the hydrous ferric oxides to form solid precipitates and the coagulation of the precipitates to form flocs large enough to settle out of solution. FIGS. 10(a) through 11(b) represents the amount of As removed by the mucilage over time for the optimized initial conditions of 50 mg/L Fe, 100 mg/L mucilage and As challenge of 100 μg/L. The process was rapid, achieving equilibrium within 30 minutes and the majority of removal achieved in 10-15 minutes. There was some variation observed in the equilibrium endpoint; removal at 24 h ranged from 75 to 96%. This may be due to different extents of hydrolysis of the dissolved Fe(III) salt. This was supported when fresh, unhydrolysed Fe(III) solution was added, exhibiting a lower removal percentage of As, as seen in FIG. 12. The shape of the kinetic curve speaks to the adsorption of the iron arsenate precipitate particles on the mucilage surface; equilibrium is achieved when no more surface sites are available or can be accessed by the precipitate. I was noted that adding previously hydrolyzed Fe salt, i.e. aged or pre-hydrolyzed, was advantageous, as the previously hydrolyzed Fe salt immediately interacted with As, whereas fresh Fe salt solutions, i.e. un-aged, provided a lower removal due to a lower extent of hydrolysis. While the optimal hydrolysis time was not determined, the greater the extent of hydrolysis, the more improved the removal. Therefore, hydrolysis extending beyond 24 hours is advantageous. Moreover, the adsorption time is limited by the settling of the mucilage which sinks faster as it gets heavier with adsorbed iron arsenate.

Example 7

Figure 13:
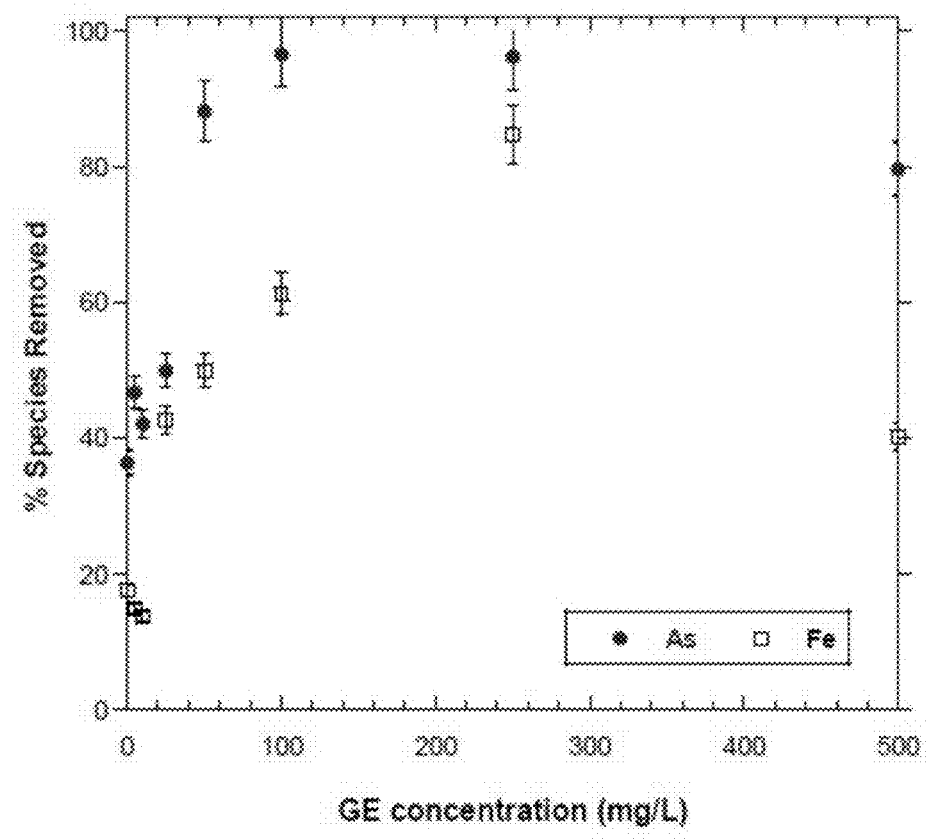
FIG. 13 is a graph showing removal of As and Fe as a function of mucilage concentration. The optimum removal occurred at 100 mg/L mucilage. Initial As concentration: 100 μg/L; initial Fe concentration: 50 mg/L; initial pH: 6.5.

Mucilage concentration was varied to deduce the optimal mucilage dosage at high (50 mg/L) and low (5 mg/L) Fe concentrations. Solutions of 100 μg/L As were prepared, as described in the previous examples. At Fe concentrations of 50 mg/L, As removal increased with increasing mucilage concentration reaching a maximum of 96% removed at 100 mg/L GE, then decreasing slightly with further increase in mucilage concentration, as seen in FIG. 13. It is interesting that further increases in mucilage concentration beyond 100 mg/L were disadvantageous to As removal, probably due to the higher mucilage concentrations causing a vertical accumulation of mucilage in the water column and so preventing efficient settling. At Fe concentrations of 5 mg/L, there was lower As removal, between 10-20%, which did not correlate with mucilage concentration. The results indicate that precipitate formation is the controlling step in the process; the mucilage appears to provide a framework or surface on which precipitate nuclei can aggregate and form larger flocs. In these experiments, the As challenge was 100 μg/L so at the best performance the As residual was less than 10 μg/L which is the maximum contaminant level proposed by the WHO.

Figure 14:
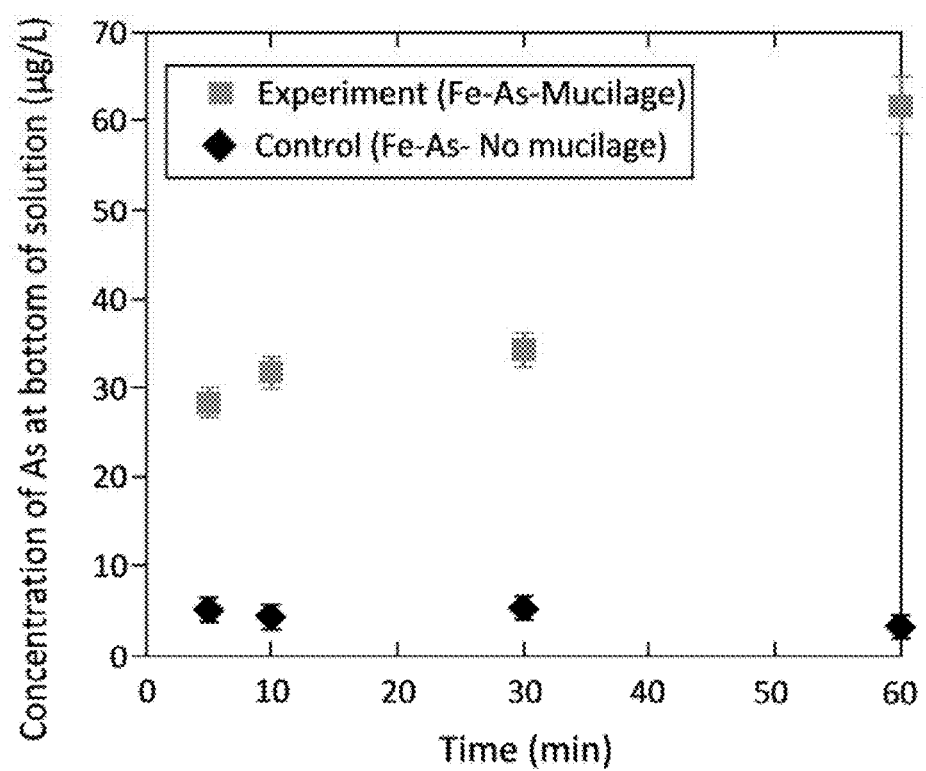
FIG. 14 is a graph showing a comparison of mucilage-treated solutions with solutions treated with Fe only. Concentrations are 1:10 dilutions of samples taken from bottom of tubes. Initial As concentration: 100 μg/L; initial Fe concentration: 50 mg/L; initial pH: 6.5, GE concentration 100 mg/L.
Figure 15:
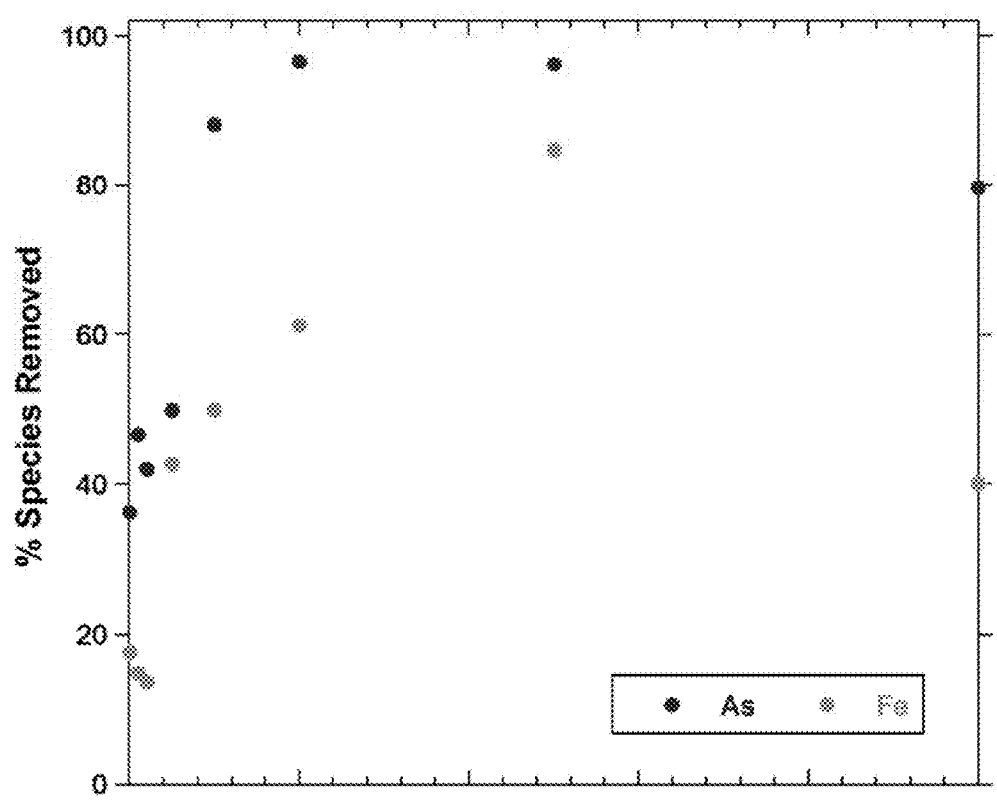
FIG. 15 is a graph showing As removal as a function of GE concentration.

The role of the mucilage was best seen by comparing the As concentrations at the bottom of the tubes of mucilage treated solutions with those treated with only Fe, as seen in FIG. 14. The increase in As concentration over time correlates to the settling of the iron-arsenate by the mucilage. By contrast, the As concentration remained fairly constant over that time period in the solutions treated with Fe only, as discussed in pervious examples. By comparison, in samples treated with ferric salt and mucilage, arsenic removal increased with increasing mucilage and Fe (III) concentrations, seen in FIG. 15. In both instances, optimal concentrations were observed beyond which, there was no further improvement in performance. The total As removal was dependent on the extent of hydrolysis of the Fe (III) salt. Fe(III) salt hydrolyses to form iron hydroxides that react with dissolved arsenate forming iron arsenate precipitates. However, cactus mucilage causes rapid floc aggregation and settling of the precipitate.

Example 8

Figure 16:
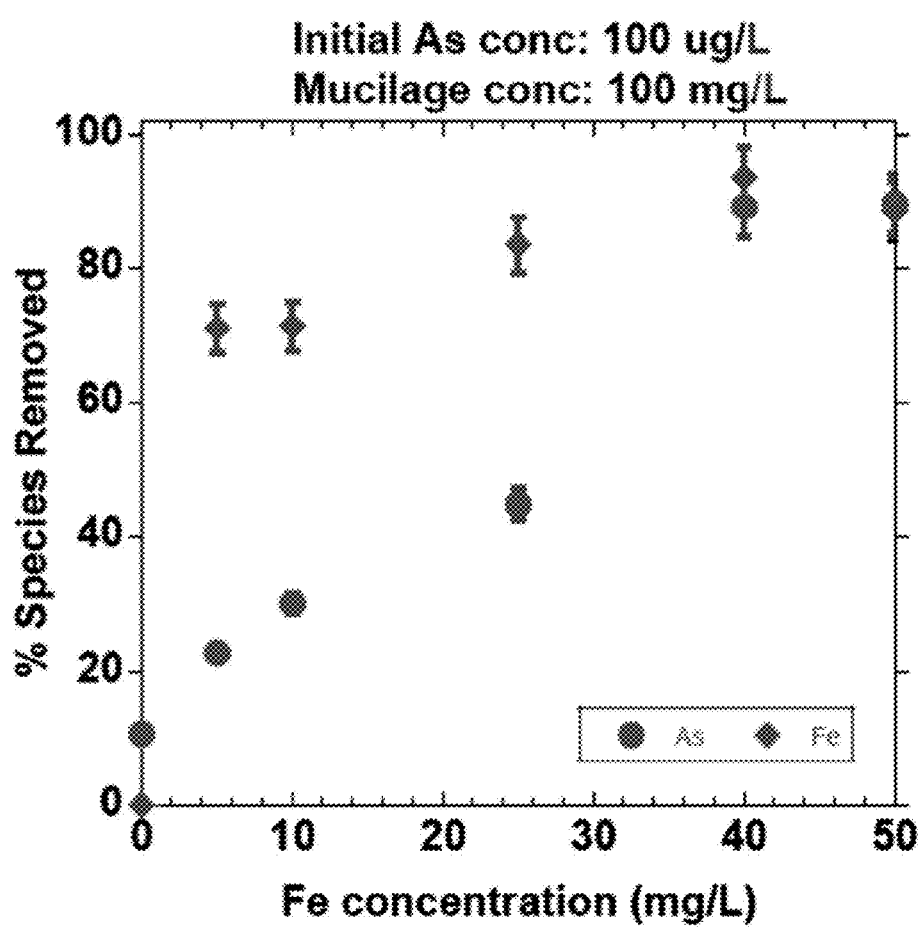
FIG. 16 is a graph showing removal of As and Fe as a function of Fe concentration. The optimum removal occurred at 40 mg/L Fe. Initial As concentration: 100 μg/L; GE concentration: 100 mg/L; initial pH: 6.5.
Figure 17:
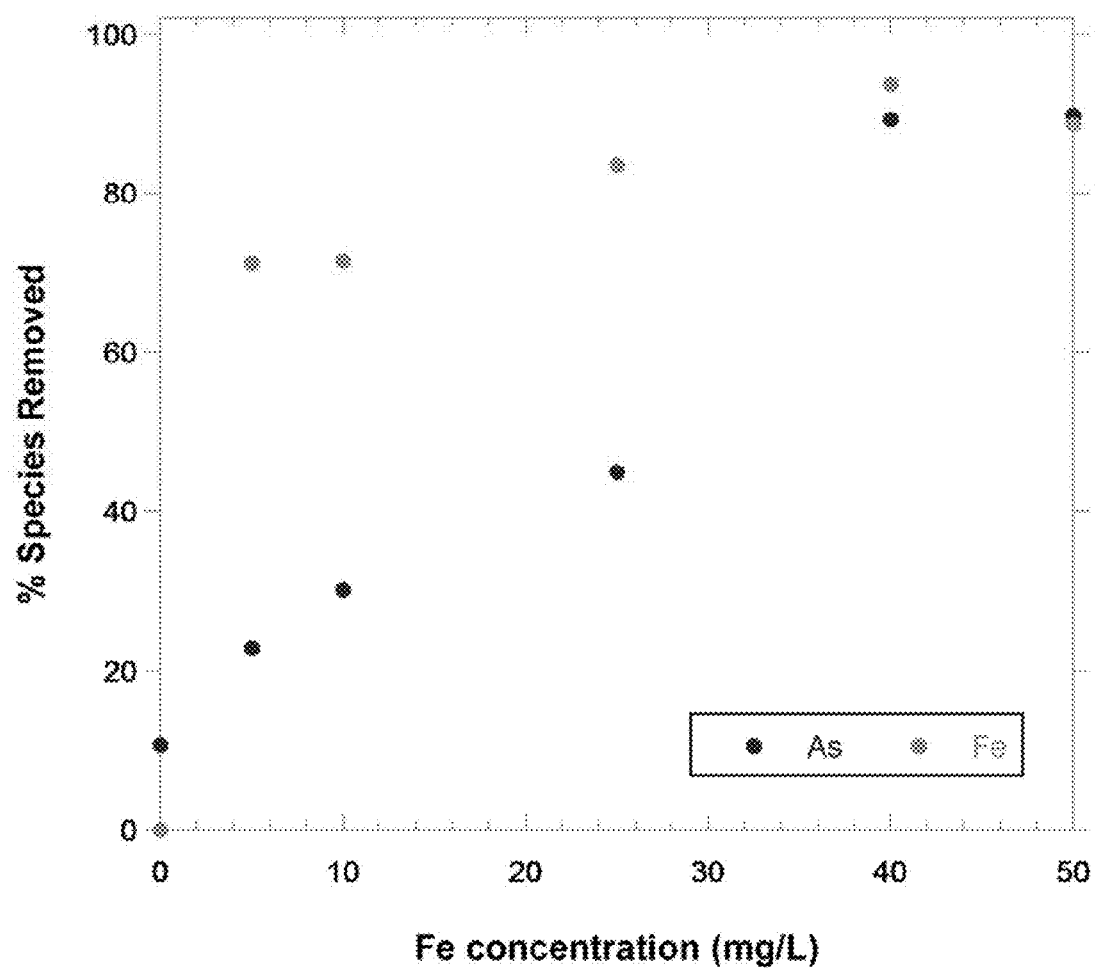
FIG. 17 is a graph showing As removal as a function of Fe(III) concentration.

The effect of iron (Fe) concentration was also studied. Solutions of 100 µg/L As were prepared, as described in the previous examples. The effect of increasing the Fe dosage from 5 to 50 mg/L is shown in FIG. 16. As expected, As removal increased linearly with increasing Fe concentration, reaching a maximum of 90% removal when the GE extract was at 100 mg/L. Further increasing the Fe concentration did not yield greater As removal, decreasing slightly with further increase in mucilage concentration. It is interesting that further increases in mucilage concentration beyond 100 mg/L were disadvantageous to As removal. This is probably due to the higher mucilage concentrations causing a vertical accumulation of mucilage in the water column and so preventing efficient settling. At Fe concentrations of 5 mg/L, there was lower As removal, between 10-20% which did not correlate with mucilage concentration. These results are shown in FIG. 17. These results indicate mucilage appears to provide a framework or surface on which precipitate nuclei can aggregate and form larger flocs.

These results indicate that forming the iron arsenate precipitate is the controlling step in the process. The maximum removal was most likely reached because the available As was limited by mass transfer. The Fe residuals ranged from the best (lowest) value of 7.5 mg/L at 250 mg/L GE, to 43 mg/L at 5 mg/L GE. The United States Environmental Protection Agency (USEPA) has set the secondary maximum contaminant level for Fe at 0.3 mg/L (Pontius. A current look at the federal drinking water regulations. *Journal of the American Water Works Association* 1992, 3, 36-50). While it is not a toxic pollutant, dissolved Fe imparts a metallic taste and smell to potable water which makes it unpalatable. These residual Fe concentrations can be lowered to potable range by a rough filter such as a sand or cloth filter.

Cactus mucilage effectively removes arsenate from water, after treatment with hydrolyzed ferric salt, by coagulation and flocculation of the colloidal ferric-arsenate complex. The ferric salt forms hydrous ferric oxides which react with the arsenate, forming the colloidal ferric-arsenate. This colloidal suspension was stable (did not settle) for more than two weeks when it was not treated with mucilage. When mucilage is added, the system showed 75-96% arsenate removal in 1 hour, while longer retention times showed 100% removal at about 1 week, as seen in FIGS. 10(a) through 11(b). At short time intervals, As removal shows an exponential reduction indicative of a diffusion-controlled process, which is the formation of the iron arsenate-mucilage complex. At intermediate times, As removal is independent of time suggesting the flocculation and settling process occurs and continues. At longer times, As removal results from further hydrolysis of the Fe (III) salt and its interaction with arsenate.

The lace-like polymer network of GE mucilage sorbs the iron arsenate precipitate forming large flocs which settle rapidly; the mucilage acts as a coagulant aid. Testing of water samples with 100 µg/L arsenate and varying amounts of ferric salt and mucilage were tested. The system showed useful performance at a mucilage concentration of 100 mg/L and Fe(III) concentration of 40 mg/L when the initial concentration of arsenate was 100 µg/L and neutral pH. Arsenic removal increases with mucilage concentration, in part, and iron concentration, and is dependent on Fe(III) hydrolysis. Cactus mucilage and iron (III) salt form the basis of a viable technology for arsenic removal from water. Without being bound to any specific theory. the proposed mechanism for arsenic removal is

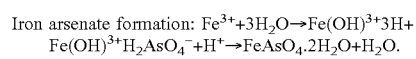

Iron arsenate formation: $Fe^{3+}+3H_2O \rightarrow Fe(OH)^{3+}3H+$
$Fe(OH)^{3+}H_2AsO_4^-+H^+ \rightarrow FeAsO_4.2H_2O+H_2O$.

The speed of the flocculation and settling of the solutions with mucilage translates to greater time efficiency and throughput of As removal systems. Further, the relative inexpensiveness and ready availability of the mucilage makes it a potentially competitive alternative to synthetic organic polymers used to enhance coagulation.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method of treating prolapse and hernias and polymer-silicon carbide surgical mesh, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of removing arsenic contamination from a sample of water, comprising:
   obtaining a sample of water, wherein the sample of water is contaminated with arsenic;
   dosing the sample of water with a ferric salt prior to addition of a gelling extract from a cactus;
   allowing the ferric salt to interact with the arsenic;
   adding the gelling extract obtained from the cactus to the sample of water after dosing the sample of water with the ferric salt and allowing the ferric salt to interact with the arsenic, where the gelling extract is obtained by the steps further comprising:
   obtaining cactus pads;
   dicing and boiling the cactus pads;
   liquidizing the cactus pads and adding a base to neutralize the liquidized cactus pads;
   centrifuging the liquidized cactus pads into a liquid fraction and a solid precipitate;
   collecting the solid precipitate;

adding sodium hexametaphosphate to the solid precipitate and mixing;
filtering the solid precipitate;
resuspending the solid precipitate in water to form a suspension;
lowering the pH of the suspension;
precipitating a mucilage precipitate from the suspension;
resuspending the mucilage precipitate with deionized water and adjusting the pH until the mucilage precipitate dissolves;
filtering the dissolved mucilage precipitate to form the gelling extract;
mixing the sample of water and gelling extract; and
allowing the sample of water to cure, wherein during the curing step arsenic precipitates out of the sample of water.

2. The method of claim 1, wherein the gelling extract is added at a final concentration of between about 50 and about 500 mg/L.

3. The method of claim 2, wherein the gelling extract is at a final concentration of between about 100 mg/L and about 200 mg/L.

4. The method of claim 2, wherein the gelling extract is at a final concentration of 100 mg/L.

5. The method of claim 1, wherein the ferric salt is ferric nitrate, ferric chloride, ferric sulfate, ferric carbonate, ferric gluconate, ferric oxalate, or saccharated ferric oxide.

6. The method of claim 5, wherein the ferric salt is dosed at a final concentration of between about 6 mg/L and about 50 mg/L.

7. The method of claim 6, wherein the ferric salt is at a final concentration of between about 26 mg/L and about 50 mg/L.

8. The method of claim 7, wherein the ferric salt at a final concentration of between about 40 mg/L and about 50 mg/L.

9. The method of claim 1, further comprising allowing the sample of water and added ferric salt and added gelling extract to stand for at least 10 min.

10. The method of claim 9, wherein the water and added ferric salt and added gelling extract stands for about 1 hour.

11. The method of claim 9, wherein the water and added ferric salt and added gelling extract stands for about 24 h.

12. The method of claim 1, further comprising filtering residual iron and mucilage from the sample of water further comprising:
collecting the sample of water after precipitation of arsenic; and
running the sample of water through filter cloth, filter paper, Buchner funnel, rotary vacuum-drum filter, screen filter, sand filter, fine mesh sieve, coffee filter, ceramic membrane size-exclusion filter, cellulose acetate membrane size-exclusion filter, polyvinylidene fluoride membrane size-exclusion filter, polyacrylonitrile membrane size-exclusion filter, polypropylene membrane size-exclusion filter, polysulfone membrane size-exclusion filter, polyethersulfone membrane size-exclusion filter, polyamide membrane size-exclusion filter, hollow fiber filter, or a combination thereof in sequence.

13. The method of claim 1, further comprising hydrolyzing the ferric salt prior to addition to the sample of water.

14. The method of claim 13, wherein the ferric salt is aged in water for at least 48 hours to hydrolyze the ferric salt.

15. A method of removing arsenic contamination from a sample of water, comprising:
obtaining a sample of water, wherein the sample of water is co, urinated with arsenic;
dosing the sample of water with a hydrolyzed ferric salt, wherein the hydrolyzed ferric salt is obtained by aging ferric salt in water for at least 48 hours prior to addition to the sample of water;
allowing the hydrolyzed ferric salt to interact with the arsenic;
adding a gelling extract obtained from cactus to the sample of water after dosing the sample of water with the hydrolyzed ferric salt, where the gelling extract is obtained by the steps further comprising:
obtaining cactus pads;
dicing and boiling the cactus pads;
liquidizing the cactus pads and adding a base to neutralize the liquidized cactus pad;
centrifuging the liquidized cactus pads into a liquid fraction and a solid precipitate;
collecting the solid precipitate;
adding sodium hexametaphosphate to the solid precipitate and mixing;
filtering the solid precipitate;
resuspending the solid precipitate in water to form a suspension;
lowering the pH of the suspension;
precipitating a mucilage precipitate from the suspension;
resuspending the mucilage precipitate with deionized water and adjusting the pH until the mucilage precipitate dissolves;
filtering the dissolved mucilage precipitate to form the gelling extract;
wherein the gelling extract is added at a final concentration of between about 50 and about 500 mg/L;
mixing the sample of water and gelling extract; and
allowing the sample of water to cure, wherein during the curing step arsenic precipitates out of the sample of water.

16. The method of claim 15, wherein the gelling extract is at a final concentration of 100 mg/L.

17. The method of claim 15, wherein the ferric salt is ferric nitrate, ferric chloride, ferric sulfate, ferric carbonate, ferric gluconate, ferric oxalate, or saccharated ferric oxide.

18. The method of claim 17, wherein the ferric salt is at a final concentration of between about 40 mg/L and about 50 mg/L.

19. The method of claim 15, further comprising allowing the sample of water, added hydrolyzed ferric salt, and added gelling extract to stand for at least 10 min.

20. The method of claim 19, wherein the water and added hydrolyzed ferric salt and added gelling extract to stand for about 24 h.

21. The method of claim 15, further comprising filtering residual iron and mucilage from the sample of water further comprising:
collecting the sample of water after precipitation of arsenic; and
running the sample of water through filter cloth, filter cloth, filter paper, Buchner funnel, rotary vacuum-drum filter, screen filter, sand filter, fine mesh sieve, coffee filter, ceramic membrane size-exclusion filter, cellulose acetate membrane size-exclusion filter, polyvinylidene fluoride membrane size-exclusion filter, polyacrylonitrile membrane size-exclusion filter, polypropylene membrane size-exclusion filter, polysulfone membrane size-exclusion filter, polyethersulfone membrane size-exclusion filter, polyamide membrane size-exclusion filter, hollow fiber filter, or a combination thereof in sequence.

* * * * *